US012378559B2

(12) United States Patent
Brooke et al.

(10) Patent No.: US 12,378,559 B2
(45) Date of Patent: Aug. 5, 2025

(54) ENZYMATIC NUCLEIC ACID MOLECULES

(71) Applicant: UNIVERSITY OF ESSEX ENTERPRISES LIMITED, Essex (GB)

(72) Inventors: Greg Brooke, Essex (GB); Antonio Marco Castillo, Essex (GB); Angela Pine, Essex (GB)

(73) Assignee: UNIVERSITY OF ESSEX ENTERPRISES LIMITED, Essex (GB)

( * ) Notice: Subject to any disclaimer, the term of this patent is extended or adjusted under 35 U.S.C. 154(b) by 1127 days.

(21) Appl. No.: 17/290,119

(22) PCT Filed: Oct. 31, 2019

(86) PCT No.: PCT/GB2019/053103
§ 371 (c)(1),
(2) Date: Apr. 29, 2021

(87) PCT Pub. No.: WO2020/089646
PCT Pub. Date: May 7, 2020

(65) Prior Publication Data
US 2021/0395753 A1  Dec. 23, 2021

(30) Foreign Application Priority Data
Nov. 2, 2018  (GB) ..................................... 1817990

(51) Int. Cl.
*C12N 15/113*  (2010.01)
*A61P 35/00*  (2006.01)

(52) U.S. Cl.
CPC .......... *C12N 15/1138* (2013.01); *A61P 35/00* (2018.01); *C12N 2310/127* (2013.01); *C12N 2310/3231* (2013.01); *C12N 2310/335* (2013.01); *C12N 2320/32* (2013.01)

(58) Field of Classification Search
CPC .......... C12N 15/1138; C12N 2310/127; C12N 2310/3231; C12N 2310/335; C12N 2320/32; A61P 35/00
See application file for complete search history.

(56) References Cited

U.S. PATENT DOCUMENTS

| 7,704,965 | B2 * | 4/2010 | Clawson | C12N 7/00 435/5 |
|---|---|---|---|---|
| 9,970,040 | B2 | 5/2018 | Elbaz et al. | |
| 2002/0177568 | A1 | 11/2002 | Stinchcomb et al. | |
| 2003/0064946 | A1 | 4/2003 | McSwiggen et al. | |
| 2003/0073207 | A1 | 4/2003 | Akhtar et al. | |
| 2003/0077639 | A1 | 4/2003 | Roy et al. | |
| 2003/0105051 | A1 | 6/2003 | McSwiggen | |
| 2003/0148971 | A1 | 8/2003 | Handel et al. | |
| 2003/0171311 | A1 | 9/2003 | Blatt et al. | |
| 2003/0203870 | A1 | 10/2003 | Blatt et al. | |
| 2004/0054156 | A1 | 3/2004 | Draper et al. | |
| 2004/0077565 | A1 | 4/2004 | Pavco et al. | |
| 2004/0102389 | A1 | 5/2004 | Pavco et al. | |
| 2004/0127446 | A1 | 7/2004 | Blatt et al. | |
| 2004/0220128 | A1 | 11/2004 | Pavco et al. | |
| 2005/0080031 | A1 | 4/2005 | McSwiggen | |
| 2007/0026394 | A1 | 2/2007 | Blatt et al. | |
| 2007/0042029 | A1 | 2/2007 | Pavco et al. | |
| 2010/0249216 | A1 | 9/2010 | Sel et al. | |

FOREIGN PATENT DOCUMENTS

| CA | 2403243 | 3/2001 |
| CA | 2442092 | 10/2002 |
| CN | 1261920 | 8/2000 |
| CN | 101932709 | 12/2010 |
| CN | 103627709 | 3/2014 |
| EP | 1767632 | 3/2007 |
| JP | 2003-506078 | 2/2003 |
| JP | 2004-512810 | 4/2004 |
| JP | 2004-532022 | 10/2004 |
| JP | 2005-537028 | 12/2005 |
| WO | WO 01/11023 | 2/2001 |
| WO | WO 01/30394 | 5/2001 |
| WO | WO 01/32846 | 5/2001 |
| WO | WO 01/59103 | 8/2001 |
| WO | WO 01/62911 | 8/2001 |
| WO | WO 02/11674 | 2/2002 |

(Continued)

OTHER PUBLICATIONS

Chen et al., "Catalytic Cleavage of the Androgen Receptor Messenger RNA and Functional Inhibition of Androgen Receptor Activity by a Hammerhead Ribozyme," Molecular Endocrinology, vol. 12, No. 10, Oct. 1, 1998, pp. 1558-1566.

Dass et al., "DNAzyme technology and cancer therapy: cleave and let die," Molecular Cancer Therapeutics, vol. 7, No. 2, Feb. 1, 2008, pp. 243-251.

Tong et al., "Effects of blocking androgen receptor expression with specific hammerhead ribozyme on in vitro growth of prostate cancer cell line," Chinese Medical Journal, vol. 116, No. 10, 2003, pp. 1515-1518.

Zegarra-Moro et al., "Disruption of Androgen Receptor Function Inhibits Proliferation of Androgen-refractory Prostate Cancer Cells," Cancer Research, vol. 62, Feb. 15, 2002, pp. 1008-1013.

International Search Report and Written Opinion for International (PCT) Patent Application No. PCT/GB2019/053103, dated Mar. 31, 2020, 18 pages.

(Continued)

*Primary Examiner* — Aaron J Kosar
(74) *Attorney, Agent, or Firm* — Sheridan Ross PC

(57) ABSTRACT

Certain aspects of the present invention relate to methods and reagents for the treatment of prostate cancer. Also included in the present invention is an enzymatic nucleic acid molecule ("DNAzyme") comprising a catalytic core and two specific binding arms complementary to a nucleic acid sequence comprised in an Androgen Receptor mRNA molecule. Also included are compositions comprising the enzymatic nucleic acid molecules and methods of treating disorders such as prostate cancer comprising use of such nucleic acid molecules.

10 Claims, 6 Drawing Sheets

Specification includes a Sequence Listing.

(56) References Cited

FOREIGN PATENT DOCUMENTS

WO      WO 02/68637      9/2002
WO      WO 2004/002416      1/2004

OTHER PUBLICATIONS

International Preliminary Report on Patentability for International (PCT) Application No. PCT/GB2019/053103, dated May 14, 2021, 12 pages.
Search Report for United Kingdom Patent Application No. 1817990.3, dated Apr. 9, 2019, 4 pages.
Hollenstein, "DNA Catalysis: The Chemical Repertoire of DNAzymes," Molecules, vol. 20, No. v 20, 2015, pp. 20777-20804.
Santoro et al., "A general purpose RNA-cleaving DNA enzyme," Proc. Natl. Acad. Sci. USA, vol. 94, Apr. 1997, pp. 4262.
Chang et al., "Antisense down regulation of connexin31.1 reduces apoptosis and increases thickness of human and animal corneal epithelia," Cell Biology International, vol. 33, 2009, pp. 376-385.
Official Action (with English translation) for Japan Patent Application No. 2021-524200, dated Sep. 19, 2023, 12 pages.
Clawson et al. "Inhibition of papilloma progression by antisense oligonucleotides targeted to HPV11 E6/E7 RNA," Gene Therapy, Sep. 2004, vol. 11, No. 17, pp. 1331-1341.

\* cited by examiner

Figure 3

| DNAzyme | Sequence Identity No. | Sequence | Cleavage |
|---|---|---|---|
| DZAR3 | 1 | GTAGAGAGAGGCTAGCTACAACGAAGGGTAGAC | 100% |
| DZAR18 | 2 | CAGGGTAGAGGCTAGCTACAACGAGGCAGTTCA | 99% |
| DZAR15 | 3 | CAGGGCCGAGGCTAGCTACAACGATGCGGCTGT | 95% |
| DZAR8 | 4 | ACCACCACAGGCTAGCTACAACGAGGTCCATAC | 93% |
| DZAR34 | 5 | CTTCGGATAGGCTAGCTACAACGATGCTTCCTG | 92% |
| DZAR24 | 6 | CGGTCCATAGGCTAGCTACAACGAAACTGGCCT | 91% |
| DZAR23 | 7 | TCCATACAAGGCTAGCTACAACGATGGCCTTCT | 90% |
| DZAR28 | 8 | CCACCACCAGGCTAGCTACAACGACACACGGTC | 90% |
| DZAR27 | 9 | CCACCACCAGGCTAGCTACAACGAACGGTCCAT | 89% |
| DZAR25 | 10 | CACGGTCCAGGCTAGCTACAACGAACAACTGGC | 85% |
| DZAR7 | 11 | GCCTTCGGAGGCTAGCTACAACGAACTGCTTCC | 85% |
| DZAR29 | 12 | CCCCCACCAGGCTAGCTACAACGACACCACACG | 82% |
| DZAR5 | 13 | GGTAGACGGGGCTAGCTACAACGAAGTTCAAGT | 79% |
| DZAR9 | 14 | CGCTTTTGAGGCTAGCTACAACGAACAAGTGGG | 79% |
| DZAR19 | 15 | CAAGTGGGAGGCTAGCTACAACGATGGGATAGG | 75% |
| DZAR14 | 16 | GGCCGACTGGGCTAGCTACAACGAGGCTGTGAA | 53% |
| DZAR21 | 17 | CTTTTGACAGGCTAGCTACAACGAAAGTGGGAC | 48% |
| DZAR33 | 18 | CGGATACTGGGCTAGCTACAACGATTCCTGCTG | 38% |
| DZAR13 | 19 | CGACTGCGGGGCTAGCTACAACGATGTGAAGGT | 29% |
| DZAR16 | 20 | ACTCCAGGGGCTAGCTACAACGACGACTGCGG | 28% |
| DZAR1 | 21 | CTGCGGCTGGGCTAGCTACAACGAGAAGGTTGC | 24% |
| DZAR20 | 22 | TGACACAAGGGCTAGCTACAACGAGGGACTGGG | 23% |
| DZAR2 | 23 | GAGACAGGGGGCTAGCTACAACGAAGACGGCAG | 12% |
| DZAR26 | 24 | ACCACACGGGCTAGCTACAACGACCATACAAC | 9% |
| DZAR4 | 25 | AGGTTGCTGGGCTAGCTACAACGATCCTCATCC | 8% |
| DZAR10 | 26 | CGCTCAGGAGGCTAGCTACAACGAGTCTTTAAG | 3% |
| DZAR11 | 27 | TGAAGGTTGGGCTAGCTACAACGATGTTCCTCA | 0% |
| DZAR12 | 28 | CTGTGAAGGGGCTAGCTACAACGATGCTGTTCC | 0% |
| DZAR17 | 29 | AGACGGCAGGGCTAGCTACAACGATCAAGTGTC | 0% |
| DZAR22 | 30 | CCCATTTCGGGCTAGCTACAACGATTTTGACAC | 0% |
| DZAR30 | 31 | TCTTTAAGGGGCTAGCTACAACGACAGCGGAGC | 0% |
| DZAR31 | 32 | CTCAGGATGGGCTAGCTACAACGACTTTAAGGT | 0% |
| DZAR32 | 33 | CTGGCCTCGGGCTAGCTACAACGATCAGGATGT | 0% |

SEQUENCE LISTING

```
<160> NUMBER OF SEQ ID NOS: 34

<210> SEQ ID NO 1
<211> LENGTH: 33
<212> TYPE: DNA
<213> ORGANISM: Artificial Sequence
<220> FEATURE:
<223> OTHER INFORMATION: Enzymatic Nucleic Acid Molecule

<400> SEQUENCE: 1
gtagagagag gctagctaca acgaagggta gac                                   33

<210> SEQ ID NO 2
<211> LENGTH: 33
<212> TYPE: DNA
<213> ORGANISM: Artificial Sequence
<220> FEATURE:
<223> OTHER INFORMATION: Enzymatic Nucleic Acid Molecule

<400> SEQUENCE: 2
cagggtagag gctagctaca acgaggcagt tca                                   33

<210> SEQ ID NO 3
<211> LENGTH: 33
<212> TYPE: DNA
<213> ORGANISM: Artificial Sequence
<220> FEATURE:
<223> OTHER INFORMATION: Enzymatic Nucleic Acid Molecule

<400> SEQUENCE: 3
cagggccgag gctagctaca acgatgcggc tgt                                   33

<210> SEQ ID NO 4
<211> LENGTH: 33
<212> TYPE: DNA
<213> ORGANISM: Artificial Sequence
<220> FEATURE:
<223> OTHER INFORMATION: Enzymatic Nucleic Acid Molecule

<400> SEQUENCE: 4
accaccacag gctagctaca acgaggtcca tac                                   33
```

```
<210> SEQ ID NO 5
<211> LENGTH: 33
<212> TYPE: DNA
<213> ORGANISM: Artificial Sequence
<220> FEATURE:
<223> OTHER INFORMATION: Enzymatic Nucleic Acid Molecule

<400> SEQUENCE: 5
cttcggatag gctagctaca acgatgcttc ctg                             33

<210> SEQ ID NO 6
<211> LENGTH: 33
<212> TYPE: DNA
<213> ORGANISM: Artificial Sequence
<220> FEATURE:
<223> OTHER INFORMATION: Enzymatic Nucleic Acid Molecule

<400> SEQUENCE: 6
cggtccatag gctagctaca acgaaactgg cct                             33

<210> SEQ ID NO 7
<211> LENGTH: 33
<212> TYPE: DNA
<213> ORGANISM: Artificial Sequence
<220> FEATURE:
<223> OTHER INFORMATION: Enzymatic Nucleic Acid Molecule

<400> SEQUENCE: 7
tccatacaag gctagctaca acgatggcct tct                             33

<210> SEQ ID NO 8
<211> LENGTH: 33
<212> TYPE: DNA
<213> ORGANISM: Artificial Sequence
<220> FEATURE:
<223> OTHER INFORMATION: Enzymatic Nucleic Acid Molecule

<400> SEQUENCE: 8
ccaccaccag gctagctaca acgacacacg gtc                             33

<210> SEQ ID NO 9
<211> LENGTH: 33
<212> TYPE: DNA
<213> ORGANISM: Artificial Sequence
<220> FEATURE:
<223> OTHER INFORMATION: Enzymatic Nucleic Acid Molecule

<400> SEQUENCE: 9
ccaccaccag gctagctaca acgaacggtc cat                             33

<210> SEQ ID NO 10
<211> LENGTH: 33
<212> TYPE: DNA
<213> ORGANISM: Artificial Sequence
<220> FEATURE:
<223> OTHER INFORMATION: Enzymatic Nucleic Acid Molecule

<400> SEQUENCE: 10
cacggtccag gctagctaca acgaacaact ggc                             33

<210> SEQ ID NO 11
<211> LENGTH: 33
<212> TYPE: DNA
<213> ORGANISM: Artificial Sequence
<220> FEATURE:
<223> OTHER INFORMATION: Enzymatic Nucleic Acid Molecule
```

<400> SEQUENCE: 11
gccttcggag gctagctaca acgaactgct tcc					33

<210> SEQ ID NO 12
<211> LENGTH: 33
<212> TYPE: DNA
<213> ORGANISM: Artificial Sequence
<220> FEATURE:
<223> OTHER INFORMATION: Enzymatic Nucleic Acid Molecule

<400> SEQUENCE: 12
cccccaccag gctagctaca acgacaccac acg					33

<210> SEQ ID NO 13
<211> LENGTH: 33
<212> TYPE: DNA
<213> ORGANISM: Artificial Sequence
<220> FEATURE:
<223> OTHER INFORMATION: Enzymatic Nucleic Acid Molecule

<400> SEQUENCE: 13
ggtagacggg gctagctaca acgaagttca agt					33

<210> SEQ ID NO 14
<211> LENGTH: 33
<212> TYPE: DNA
<213> ORGANISM: Artificial Sequence
<220> FEATURE:
<223> OTHER INFORMATION: Enzymatic Nucleic Acid Sequence

<400> SEQUENCE: 14
cgcttttgag gctagctaca acgaacaagt ggg					33

<210> SEQ ID NO 15
<211> LENGTH: 33
<212> TYPE: DNA
<213> ORGANISM: Artificial Sequence
<220> FEATURE:
<223> OTHER INFORMATION: Enzymatic Nucleic Acid Molecule

<400> SEQUENCE: 15
caagtgggag gctagctaca acgatgggat agg					33

<210> SEQ ID NO 16
<211> LENGTH: 33
<212> TYPE: DNA
<213> ORGANISM: Artificial Sequence
<220> FEATURE:
<223> OTHER INFORMATION: Enzymatic Nucleic Acid Molecule

<400> SEQUENCE: 16
ggccgactgg gctagctaca acgaggctgt gaa					33

<210> SEQ ID NO 17
<211> LENGTH: 33
<212> TYPE: DNA
<213> ORGANISM: Artificial Sequence
<220> FEATURE:
<223> OTHER INFORMATION: Enzymatic Nucleic Acid Molecule

<400> SEQUENCE: 17
cttttgacag gctagctaca acgaaagtgg gac					33

<210> SEQ ID NO 18
<211> LENGTH: 33

```
<212> TYPE: DNA
<213> ORGANISM: Artificial Sequence
<220> FEATURE:
<223> OTHER INFORMATION: Enzymatic Nucleic Acid Molecule

<400> SEQUENCE: 18
cggatactgg gctagctaca acgattcctg ctg                          33

<210> SEQ ID NO 19
<211> LENGTH: 33
<212> TYPE: DNA
<213> ORGANISM: Artificial Sequence
<220> FEATURE:
<223> OTHER INFORMATION: Enzymatic Nucleic Acid Molecule

<400> SEQUENCE: 19
cgactgcggg gctagctaca acgatgtgaa ggt                          33

<210> SEQ ID NO 20
<211> LENGTH: 33
<212> TYPE: DNA
<213> ORGANISM: Artificial Sequence
<220> FEATURE:
<223> OTHER INFORMATION: Enzymatic Nucleic Acid Molecule

<400> SEQUENCE: 20
actccagggg gctagctaca acgacgactg cgg                          33

<210> SEQ ID NO 21
<211> LENGTH: 33
<212> TYPE: DNA
<213> ORGANISM: Artificial Sequence
<220> FEATURE:
<223> OTHER INFORMATION: Enzymatic Nucleic Acid Molecule

<400> SEQUENCE: 21
ctgcggctgg gctagctaca acgagaaggt tgc                          33

<210> SEQ ID NO 22
<211> LENGTH: 33
<212> TYPE: DNA
<213> ORGANISM: Artificial Sequence
<220> FEATURE:
<223> OTHER INFORMATION: Enzymatic Nuclear Acid Molecule

<400> SEQUENCE: 22
tgacacaagg gctagctaca acgagggact ggg                          33

<210> SEQ ID NO 23
<211> LENGTH: 33
<212> TYPE: DNA
<213> ORGANISM: Artificial Sequence
<220> FEATURE:
<223> OTHER INFORMATION: Enzymatic Nulclear Acid Molecule

<400> SEQUENCE: 23
gagacagggg gctagctaca acgaagacgg cag                          33

<210> SEQ ID NO 24
<211> LENGTH: 33
<212> TYPE: DNA
<213> ORGANISM: Artificial Sequence
<220> FEATURE:
<223> OTHER INFORMATION: Enzymatic Nuclear Acid Molecule

<400> SEQUENCE: 24
```
accacacggg gctagctaca acgaccatac aac                                33

<210> SEQ ID NO 25
<211> LENGTH: 33
<212> TYPE: DNA
<213> ORGANISM: Artificial Sequence
<220> FEATURE:
<223> OTHER INFORMATION: Enzymatic Nuclear Acid Molecule

<400> SEQUENCE: 25
aggttgctgg gctagctaca acgatcctca tcc                                33

<210> SEQ ID NO 26
<211> LENGTH: 33
<212> TYPE: DNA
<213> ORGANISM: Artificial Sequence
<220> FEATURE:
<223> OTHER INFORMATION: Enzymatic Nucleic Acid Molecule

<400> SEQUENCE: 26
cgctcaggag gctagctaca acgagtcttt aag                                33

<210> SEQ ID NO 27
<211> LENGTH: 33
<212> TYPE: DNA
<213> ORGANISM: Artificial Sequence
<220> FEATURE:
<223> OTHER INFORMATION: Enzymatic Nucleic Acid Molecule

<400> SEQUENCE: 27
tgaaggttgg gctagctaca acgatgttcc tca                                33

<210> SEQ ID NO 28
<211> LENGTH: 33
<212> TYPE: DNA
<213> ORGANISM: Artificial Sequence
<220> FEATURE:
<223> OTHER INFORMATION: Enzymatic Nuclear Acid Molecule

<400> SEQUENCE: 28
ctgtgaaggg gctagctaca acgatgctgt tcc                                33

<210> SEQ ID NO 29
<211> LENGTH: 33
<212> TYPE: DNA
<213> ORGANISM: Artificial Sequence
<220> FEATURE:
<223> OTHER INFORMATION: Enzymatic Nuclear Acid Molecule

<400> SEQUENCE: 29
agacggcagg gctagctaca acgatcaagt gtc                                33

<210> SEQ ID NO 30
<211> LENGTH: 33
<212> TYPE: DNA
<213> ORGANISM: Artificial Sequence
<220> FEATURE:
<223> OTHER INFORMATION: Enzymatic Nuclear Acid Molecule

<400> SEQUENCE: 30
cccatttcgg gctagctaca acgattttga cac                                33

<210> SEQ ID NO 31
<211> LENGTH: 33
<212> TYPE: DNA
<213> ORGANISM: Artificial Sequence

```
<220> FEATURE:
<223> OTHER INFORMATION: Enzymatic Nucleic Acid Molecule

<400> SEQUENCE: 31
tctttaaggg gctagctaca acgacagcgg agc                                    33

<210> SEQ ID NO 32
<211> LENGTH: 33
<212> TYPE: DNA
<213> ORGANISM: Artificial Sequence
<220> FEATURE:
<223> OTHER INFORMATION: Enzymatic Nucleic Acid Molecule

<400> SEQUENCE: 32
ctcaggatgg gctagctaca acgactttaa ggt                                    33

<210> SEQ ID NO 33
<211> LENGTH: 33
<212> TYPE: DNA
<213> ORGANISM: Artificial Sequence
<220> FEATURE:
<223> OTHER INFORMATION: Enzymatic Nucleic Acid Molecule

<400> SEQUENCE: 33
ctggcctcgg gctagctaca acgatcagga tgt                                    33

<210> SEQ ID NO 34
<211> LENGTH: 15
<212> TYPE: DNA
<213> ORGANISM: Artificial Sequence
<220> FEATURE:
<223> OTHER INFORMATION: Catalytic core

<400> SEQUENCE: 34
ggctagctac aacga                                                        15
```

ENZYMATIC NUCLEIC ACID MOLECULES

CROSS REFERENCE TO RELATED APPLICATIONS

This application is a national stage application under 35 U.S.C. 371 and claims the benefit of PCT Application No. PCT/GB2019/053103 having an international filing date of 31 Oct. 2019, which designated the United States, which PCT application claimed the benefit of Great Britain Patent Application No. 1817990.3 filed 2 Nov. 2018, the disclosures of each of which are incorporated herein by reference in their entireties.

REFERENCE TO SEQUENCE LISTING

This application contains a Sequence Listing submitted as an electronic text file named "Sequence_Listing-as-filed", having a size in bytes of 7,000 bytes, and created on Oct. 31, 2019. The information contained in this electronic file is hereby incorporated by reference in its entirety pursuant to 37 CFR § 1.52 (e) (5).

FIELD OF THE INVENTION

Certain aspects of the present invention relate to methods and reagents for the treatment of prostate cancer. Also included in the present invention is an enzymatic nucleic acid molecule ("DNAzyme") comprising a catalytic core and two specific binding arms complementary to a nucleic acid sequence comprised in an Androgen Receptor mRNA molecule. Also included are compositions comprising the enzymatic nucleic acid molecules and methods of treating disorders such as prostate cancer comprising use of such nucleic acid molecules.

BACKGROUND TO THE INVENTION

Prostate cancer is the most common cancer diagnosis in men and remains the third leading cause of death in men. There are on average 130 new cases of prostate cancer diagnosed every day in the UK making it the second most common cancer. Incidence rates for prostate cancer are projected to rise by 12% in the UK by 2035. Current therapeutic procedures involve surgery often coupled with radiation therapy and, in advanced cancerous stages, hormone therapy and chemotherapy. Further details of the hormone therapy are provided below.

Androgen and the Androgen Receptor (AR) play a pivotal role in expression of the male phenotype. Androgen associates with the Androgen Receptor, which is a ligand dependent transcription factor. Translocation into the cell nucleus and dimerization of the Androgen Receptor occurs upon association with androgen in the cell cytoplasm. Within the nucleus the activated Androgen Receptor binds to specific DNA sequences, referred to as the hormone response elements. The Androgen Receptor signalling pathway culminates in the up or down regulation of specific genes.

Prostate cancer is associated with alterations in Androgen Receptor functions. The Androgen Receptor signalling pathway is a fundamental process in the growth of many cancers and in particular prostate cancer. Current methods of treating prostate cancer take advantage of this androgen dependence by disrupting the signalling pathway to inhibit tumour growth.

Resistance to these treatments can still occur as the Androgen Receptor may undergo an alternative splicing event or incur mutations advantageous to cancer growth. Therefore, designing novel therapeutic strategies to down regulate the multiple forms of the Androgen Receptor and disrupt the signaling pathway is of the upmost importance. Recent therapeutic strategies have been designed to down regulate the Androgen Receptor using Ribozymes and antisense molecules.

Hormone therapy can also be conducted alone for localized prostate cancer patients who are not candidates for surgery. Hormone therapy is used to block the production or action of androgens. The current treatment regimens for prostate cancer result in multiple side effects such as decreased bone mineral density, increased risk of osteoporotic fragility fractures, weight gain and fatigue leading to a drastically reduced quality of life for the patient.

The hormonal treatment for prostate cancer, specifically androgen deprivation therapy, is initially effective in the majority of cases. However, it is not uncommon for patients to subsequently relapse and develop a more aggressive castrate resistant form of prostate cancer, rendering further hormone therapy ineffective. Therefore, there is a great need for novel therapeutic strategies to target therapy resistant disease as well as a front line treatment.

It is also considered that Androgen Receptor (AR)-mediated androgen action may also have a role in female reproductive physiology. Splice variants of the Androgen Receptor are proposed to have an etiological role in polycystic ovary syndrome (PCOS).

Enzymatic nucleic acid molecules (also referred to as deoxyribozymes, DNA enzymes or DNAzymes) are synthetic catalysts constructed from single stranded deoxyribonucleic acid polymers, which can be categorised into either 10-23 or 8-17 enzymatic nucleic acids. Enzymatic nucleic acids consist of a catalytic core flanked by two specificity sequences and have the ability to fold into intricate secondary structures. The catalytic core typically requires a divalent cation, such as $Mg^{2+}$, $Ca^{2+}$, $Pb^{2+}$, as a cofactor to be catalytically active. Currently DNAzymes have a broad range of catalytic functions with one of the most common being ribonuclease activity. The ribonuclease activity of an enzymatic nucleic acid is conducted by a transesterification reaction that occurs through an acid-base catalytic mechanism. The catalytic activity of enzymatic nucleic acid molecules may require the presence of a cofactor, namely a divalent cation which acts as a base in a transesterification reaction. The divalent cation mediates nucleophilic attack of the 2'-hydroxyl group at the adjacent phosphodiester linkage of the target RNA.

An enzymatic nucleic acid molecule with ribonuclease activity recognises its target via Watson and Crick base pairing of the flanking sequences to the target mRNA. Base complementarity recognition of the target by the flanking sequences allows for the selection and design of enzymatic nucleic acids to specific targets and therefore conducts catalysis on a specific mRNA. The specificity of enzymatic nucleic acid molecules can be employed to regulate the expression of specific genes via degradation of their transcripts and therefore impart control over certain cellular pathways, particularly those disrupted in a disease state.

Enzymatic nucleic acid molecules have an advantage over other gene expression therapeutics as they function independently of the cellular machinery, are specific to a target mRNA and possess a higher degree of chemical and also enzymatic stability. The low cost and ease of synthesis of DNA polymers is also an advantage over other therapeutic methods.

A current disadvantage of enzymatic nucleic acid molecules for therapeutic use is their dependence on relatively high concentration of divalent cations to carry out catalytic activity. Often enzymatic nucleic acid molecules exhibit little or no catalytic activity at the free divalent cation concentrations available inside cells. There is a need to develop enzymatic nucleic acid molecules that can undergo the desired rate of catalysis within physiological concentrations of divalent cations to induce a therapeutically positive outcome.

A number of enzymatic nucleic acid molecules have been developed to combat several diseases. Several of these are now undergoing clinical trials for the treatment of nodular basal-cell carcinoma, nasopharyngeal carcinoma, severe allergic bronchial asthma, atopic dermatitis and ulcerative colitis.

Currently no enzymatic nucleic acid has been designed to target the mRNA of the Androgen Receptor and therefore to treat Androgen Receptor associated disorders such as prostate cancer. Deploying an Androgen Receptor specific enzymatic nucleic acid molecule in the treatment of e.g. prostate cancer may result in halting the growth of the tumour and also have the ability to treat advanced resistant forms. Therefore, the current mutant and splice site variant forms of the Androgen Receptor will be vulnerable to the catalytic degradation of a specific enzymatic nucleic acid molecule.

It is an aim of certain embodiments of the present invention to at least partly mitigate the above-mentioned problems associated with the prior art.

It is an aim of certain embodiments of the present invention to inhibit the growth of prostate cancer.

It is an aim of certain embodiments of the present invention to provide a nucleic acid-based treatment of disorders caused by and/or associated with Androgen Receptor signalling.

It is an aim of certain embodiments of the present invention to provide a nucleic acid-based treatment of prostate cancer and other cancers.

Summary of Certain Embodiments of the Invention

In a broadest aspect, the present invention provides methods and compositions for modulating Androgen Receptor activity and for the treatment of diseases in which Androgen Receptor signalling is implicated. Aptly, aspects of the present invention provide methods and compositions for the treatment of prostate cancer. Aptly, aspects of the present invention provide methods and compositions for the treatment of polycystic ovarian syndrome.

In a further aspect, the present invention provides an enzymatic nucleic acid comprising an RNA-binding component which is designed to specifically bind to a target sequence in the Androgen Receptor gene and a catalytic core to mediate cleavage to the target RNA and therefore reduce expression of said target.

Aptly, the enzymatic nucleic acid molecule is configured to hybridize to and cleave a human androgen receptor gene product. Specifically, the enzymatic nucleic acid molecule is configured to cleave human androgen receptor mRNA.

In a first aspect of the present invention, there is provided an enzymatic nucleic acid molecule which regulates the expression of a human Androgen Receptor gene.

In some embodiments, the enzymatic nucleic acid molecule comprises a catalytic region typically around 15 nucleotides in length, although it can be appreciated that the catalytic core may be 11, 12, 13, 14, 16, 17, 18 or 19 residues in length. In certain embodiments the catalytic region is 15 nucleotides in length.

In one embodiment, the enzymatic nucleic acid molecule comprises at least one region wherein the region comprises a sequence which is complementary to a nucleic acid sequence comprised in an Androgen Receptor mRNA molecule.

In a further embodiment, the enzymatic nucleic acid molecule comprises two regions which each comprise a sequence which is complementary to a nucleic acid sequence comprised in an Androgen Receptor mRNA molecule.

In certain embodiments, the enzymatic nucleic acid molecule comprises a first region which comprises a sequence which is complementary to a nucleic acid sequence comprised in an Androgen Receptor mRNA molecule at a 5' end of the catalytic region and a second region which comprises a sequence which is complementary to a nucleic acid sequence comprised in an Androgen Receptor mRNA molecule at a 3' end of the catalytic core.

In one embodiment, the enzymatic nucleic acid molecule comprises one or more modified nucleic acid residues and/or one or more unnatural nucleic acid residues.

In certain embodiments, the enzymatic nucleic acid molecule comprises at least one Locked Nucleic Acid residue.

In one embodiment, the enzymatic nucleic acid molecule catalytically cleaves the RNA molecule upon hybridisation to an Androgen Receptor RNA molecule. In certain embodiments, the enzymatic nucleic acid molecule cleaves the Androgen Receptor RNA molecule with a cleavage efficiency of between about 50% and about 100%. For example, the catalytic cleavage event may be at least about 50%, 55%, 60%, 65%, 70%, 75%, 80%, 85%, 90%, 91%, 92%, 93%, 94%, 95%, 96%, 97%, 98%, 99% or 100% cleavage efficiency.

In a further embodiment, the enzymatic nucleic acid molecule catalytically cleaves at least 50% of Androgen Receptor RNA extracted from LNCaP cells. In a further embodiment, the enzymatic nucleic acid molecule catalytically cleaves at least 55%, e.g. 60%, 65%, 70%, 75%, 80%, 85%, 90% or 95% of Androgen Receptor RNA extracted from LNCaP cells.

In one embodiment, the enzymatic nucleic acid molecule comprises a nucleic acid sequence having at least 80% sequence identity to a nucleic acid sequence selected from;
  a. the nucleic acid sequence set forth in SEQ. ID. No 1 (DZAR3);
  b. the nucleic acid sequence set forth in SEQ. ID. No 2 (DZAR18);
  c. the nucleic acid sequence set forth in SEQ. ID. No 3 (DZAR15);
  d. the nucleic acid sequence set forth in SEQ. ID. No 4 (DZAR8);
  e. the nucleic acid sequence set forth in SEQ. ID. No 5 (DZAR34);
  f. the nucleic acid sequence set forth in SEQ. ID. No 6 (DZAR24);
  g. the nucleic acid sequence set forth in SEQ. ID. No 7 (DZAR23);
  h. the nucleic acid sequence set forth in SEQ. ID. No 8 (DZAR28);
  i. the nucleic acid sequence set forth in SEQ. ID. No 9 (DZAR27);
  j. the nucleic acid sequence set forth in SEQ. ID. No 10 (DZAR25);

k. the nucleic acid sequence set forth in SEQ. ID. No 11 (DZAR7);
l. the nucleic acid sequence set forth in SEQ. ID. No 12 (DZAR29);
m. the nucleic acid sequence set forth in SEQ. ID. No 13 (DZAR5);
n. the nucleic acid sequence set forth in SEQ. ID. No 14 (DZAR9);
o. the nucleic acid sequence set forth in SEQ. ID. No 15 (DZAR19);
p. the nucleic acid sequence set forth in SEQ. ID. No 16 (DZAR14);
q. the nucleic acid sequence set forth in SEQ. ID. No 17 (DZAR21);
r. the nucleic acid sequence set forth in SEQ. ID. No 18 (DZAR33);
s. the nucleic acid sequence set forth in SEQ. ID. No 19 (DZAR13);
t. the nucleic acid sequence set forth in SEQ. ID. No 20 (DZAR16);
u. the nucleic acid sequence set forth in SEQ. ID. No 21 (DZAR1);
v. the nucleic acid sequence set forth in SEQ. ID. No 22 (DZAR20);
w. the nucleic acid sequence set forth in SEQ. ID. No 23 (DZAR2);
x. the nucleic acid sequence set forth in SEQ. ID. No 24 (DZAR26);
y. the nucleic acid sequence set forth in SEQ. ID. No 25 (DZAR4);
z. the nucleic acid sequence set forth in SEQ. ID. No 26 (DZAR10);
aa. the nucleic acid sequence set forth in SEQ. ID. No 27 (DZAR11);
bb. the nucleic acid sequence set forth in SEQ. ID. No 28 (DZAR12);
cc. the nucleic acid sequence set forth in SEQ. ID. No 29 (DZAR17);
dd. the nucleic acid sequence set forth in SEQ. ID. No 30 (DZAR22);
ee. the nucleic acid sequence set forth in SEQ. ID. No 31 (DZAR30);
ff. the nucleic acid sequence set forth in SEQ. ID. No 32 (DZAR31); and/or
gg. the nucleic acid sequence set forth in SEQ. ID. No 33 (DZAR32).

In certain embodiments, the enzymatic nucleic acid molecule comprises a nucleic acid sequence having at least 85%, e.g. 86, 87, 88, 89, 90, 91, 92 93, 94, 95, 96, 97, 98, 99 or 100% identity with a nucleic acid sequence selected from:
a. the nucleic acid sequence set forth in SEQ. ID. No 1 (DZAR3);
b. the nucleic acid sequence set forth in SEQ. ID. No 2 (DZAR18);
c. the nucleic acid sequence set forth in SEQ. ID. No 3 (DZAR15);
d. the nucleic acid sequence set forth in SEQ. ID. No 4 (DZAR8);
e. the nucleic acid sequence set forth in SEQ. ID. No 5 (DZAR34);
f. the nucleic acid sequence set forth in SEQ. ID. No 6 (DZAR24);
g. the nucleic acid sequence set forth in SEQ. ID. No 7 (DZAR23);
h. the nucleic acid sequence set forth in SEQ. ID. No 8 (DZAR28);
i. the nucleic acid sequence set forth in SEQ. ID. No 9 (DZAR27);
j. the nucleic acid sequence set forth in SEQ. ID. No 10 (DZAR25);
k. the nucleic acid sequence set forth in SEQ. ID. No 11 (DZAR7);
l. the nucleic acid sequence set forth in SEQ. ID. No 12 (DZAR29);
m. the nucleic acid sequence set forth in SEQ. ID. No 13 (DZAR5);
n. the nucleic acid sequence set forth in SEQ. ID. No 14 (DZAR9);
o. the nucleic acid sequence set forth in SEQ. ID. No 15 (DZAR19);
p. the nucleic acid sequence set forth in SEQ. ID. No 16 (DZAR14);
q. the nucleic acid sequence set forth in SEQ. ID. No 17 (DZAR21);
r. the nucleic acid sequence set forth in SEQ. ID. No 18 (DZAR33);
s. the nucleic acid sequence set forth in SEQ. ID. No 19 (DZAR13);
t. the nucleic acid sequence set forth in SEQ. ID. No 20 (DZAR16);
u. the nucleic acid sequence set forth in SEQ. ID. No 21 (DZAR1);
v. the nucleic acid sequence set forth in SEQ. ID. No 22 (DZAR20);
w. the nucleic acid sequence set forth in SEQ. ID. No 23 (DZAR2);
x. the nucleic acid sequence set forth in SEQ. ID. No 24 (DZAR26);
y. the nucleic acid sequence set forth in SEQ. ID. No 25 (DZAR4);
z. the nucleic acid sequence set forth in SEQ. ID. No 26 (DZAR10);
aa. the nucleic acid sequence set forth in SEQ. ID. No 27 (DZAR11);
bb. the nucleic acid sequence set forth in SEQ. ID. No 28 (DZAR12);
cc. the nucleic acid sequence set forth in SEQ. ID. No 29 (DZAR17);
dd. the nucleic acid sequence set forth in SEQ. ID. No 30 (DZAR22);
ee. the nucleic acid sequence set forth in SEQ. ID. No 31 (DZAR30);
ff. the nucleic acid sequence set forth in SEQ. ID. No 32 (DZAR31); and/or
gg. the nucleic acid sequence set forth in SEQ. ID. No 33 (DZAR32).

In a further embodiment, the enzymatic nucleic acid molecule consists of a nucleic acid sequence having at least 80% sequence identity to a nucleic acid sequence selected from;
a. The nucleic acid sequence set forth in SEQ. ID. No 1 (DZAR3);
b. The nucleic acid sequence set forth in SEQ. ID. No 2 (DZAR18);
c. The nucleic acid sequence set forth in SEQ. ID. No 3 (DZAR15);
d. The nucleic acid sequence set forth in SEQ. ID. No 4 (DZAR8);
e. The nucleic acid sequence set forth in SEQ. ID. No 5 (DZAR34);
f. The nucleic acid sequence set forth in SEQ. ID. No 6 (DZAR24);

g. The nucleic acid sequence set forth in SEQ. ID. No 7 (DZAR23);
h. The nucleic acid sequence set forth in SEQ. ID. No 8 (DZAR28);
i. The nucleic acid sequence set forth in SEQ. ID. No 9 (DZAR27);
j. The nucleic acid sequence set forth in SEQ. ID. No 10 (DZAR25);
k. The nucleic acid sequence set forth in SEQ. ID. No 11 (DZAR7);
l. The nucleic acid sequence set forth in SEQ. ID. No 12 (DZAR29);
m. The nucleic acid sequence set forth in SEQ. ID. No 13 (DZAR5);
n. The nucleic acid sequence set forth in SEQ. ID. No 14 (DZAR9);
o. The nucleic acid sequence set forth in SEQ. ID. No 15 (DZAR19);
p. The nucleic acid sequence set forth in SEQ. ID. No 16 (DZAR14);
q. The nucleic acid sequence set forth in SEQ. ID. No 17 (DZAR21);
r. The nucleic acid sequence set forth in SEQ. ID. No 18 (DZAR33);
s. The nucleic acid sequence set forth in SEQ. ID. No 19 (DZAR13);
t. The nucleic acid sequence set forth in SEQ. ID. No 20 (DZAR16)
u. The nucleic acid sequence set forth in SEQ. ID. No 21 (DZAR1);
v. The nucleic acid sequence set forth in SEQ. ID. No 22 (DZAR20);
w. The nucleic acid sequence set forth in SEQ. ID. No 23 (DZAR2);
x. The nucleic acid sequence set forth in SEQ. ID. No 24 (DZAR26);
y. The nucleic acid sequence set forth in SEQ. ID. No 25 (DZAR4);
z. The nucleic acid sequence set forth in SEQ. ID. No 26 (DZAR10);
aa. The nucleic acid sequence set forth in SEQ. ID. No 27 (DZAR11);
bb. The nucleic acid sequence set forth in SEQ. ID. No 28 (DZAR12);
cc. The nucleic acid sequence set forth in SEQ. ID. No 29 (DZAR17);
dd. The nucleic acid sequence set forth in SEQ. ID. No 30 (DZAR22);
ee. The nucleic acid sequence set forth in SEQ. ID. No 31 (DZAR30);
ff. The nucleic acid sequence set forth in SEQ. ID. No 32 (DZAR31); and/or
gg. The nucleic acid sequence set forth in SEQ. ID. No 33 (DZAR32).

In certain embodiments, the enzymatic nucleic acid molecule comprises a nucleic acid sequence having at least 85%, e.g. 86, 87, 88, 89, 90, 91, 92 93, 94, 95, 96, 97, 98, 99 or 100% identity with a nucleic acid sequence selected from:
a) the nucleic acid sequence set forth in SEQ. ID. No 1 (DZAR3);
b) the nucleic acid sequence set forth in SEQ. ID. No 2 (DZAR18);
c) the nucleic acid sequence set forth in SEQ. ID. No 3 (DZAR15);
d) the nucleic acid sequence set forth in SEQ. ID. No 4 (DZAR8);
e) the nucleic acid sequence set forth in SEQ. ID. No 5 (DZAR34);
f) the nucleic acid sequence set forth in SEQ. ID. No 6 (DZAR24);
g) the nucleic acid sequence set forth in SEQ. ID. No 7 (DZAR23);
h) the nucleic acid sequence set forth in SEQ. ID. No 8 (DZAR28);
i) the nucleic acid sequence set forth in SEQ. ID. No 9 (DZAR27);
j) the nucleic acid sequence set forth in SEQ. ID. No 10 (DZAR25);
k) the nucleic acid sequence set forth in SEQ. ID. No 11 (DZAR7);
l) the nucleic acid sequence set forth in SEQ. ID. No 12 (DZAR29);
m) the nucleic acid sequence set forth in SEQ. ID. No 13 (DZAR5);
n) the nucleic acid sequence set forth in SEQ. ID. No 14 (DZAR9);
o) the nucleic acid sequence set forth in SEQ. ID. No 15 (DZAR19);
p) the nucleic acid sequence set forth in SEQ. ID. No 16 (DZAR14);
q) the nucleic acid sequence set forth in SEQ. ID. No 17 (DZAR21);
r) the nucleic acid sequence set forth in SEQ. ID. No 18 (DZAR33);
s) the nucleic acid sequence set forth in SEQ. ID. No 19 (DZAR13);
t) the nucleic acid sequence set forth in SEQ. ID. No 20 (DZAR16);
u) the nucleic acid sequence set forth in SEQ. ID. No 21 (DZAR1);
v) the nucleic acid sequence set forth in SEQ. ID. No 22 (DZAR20);
w) the nucleic acid sequence set forth in SEQ. ID. No 23 (DZAR2);
x) the nucleic acid sequence set forth in SEQ. ID. No 24 (DZAR26);
y) the nucleic acid sequence set forth in SEQ. ID. No 25 (DZAR4);
z) the nucleic acid sequence set forth in SEQ. ID. No 26 (DZAR10);
aa) the nucleic acid sequence set forth in SEQ. ID. No 27 (DZAR11);
bb) the nucleic acid sequence set forth in SEQ. ID. No 28 (DZAR12);
cc) the nucleic acid sequence set forth in SEQ. ID. No 29 (DZAR17);
dd) the nucleic acid sequence set forth in SEQ. ID. No 30 (DZAR22);
ee) the nucleic acid sequence set forth in SEQ. ID. No 31 (DZAR30);
ff) the nucleic acid sequence set forth in SEQ. ID. No 32 (DZAR31); and/or
gg) the nucleic acid sequence set forth in SEQ. ID. No 33 (DZAR32).

In another embodiment, the enzymatic nucleic acid molecule comprises a nucleic acid sequence selected from:
a. The nucleic acid sequence as set forth in SEQ. ID. No 1 (DZAR3);
b. The nucleic acid sequence as set forth in SEQ. ID. No. 2 (DZAR18);
c. The nucleic acid sequence as set forth in SEQ. ID. No. 3 (DZAR15);

d. The nucleic acid sequence as set forth in SEQ. ID. No. 4 (DZAR8);
e. The nucleic acid sequence as set forth in SEQ. ID. No. 5 (DZAR34);
f. The nucleic acid sequence as set forth in SEQ. ID. No. 6 (DZAR24);
g. The nucleic acid sequence as set forth in SEQ. ID. No. 7 (DZAR23);
h. The nucleic acid sequence as set forth in SEQ. ID. No. 8 (DZAR28);
i. The nucleic acid sequence as set forth in SEQ. ID. No. 9 (DZAR27);
j. The nucleic acid sequence as set forth in SEQ. ID. No. 10 (DZAR25);
k. The nucleic acid sequence as set forth in SEQ. ID. No. 11 (DZAR7);
l. The nucleic acid sequence as set forth in SEQ. ID. No. 12 (DZAR29);
m. The nucleic acid sequence as set forth in SEQ. ID. No. 13 (DZAR5);
n. The nucleic acid sequence as set forth in SEQ. ID. No. 14 (DZAR9);
o. The nucleic acid sequence as set forth in SEQ. ID. No. 15 (DZAR19);
p. The nucleic acid sequence as set forth in SEQ. ID. No. 16 (DZAR14); and/or
q. a nucleic acid sequence having up to four modifications e.g. 1, 2, 3 or 4 as compared to the nucleic acid sequence as set forth in SEQ. ID. No. 1, 2, 3, 4, 5, 6, 7, 8, 9, 10, 11, 12, 13, 14, 15, or 16.

In an embodiment, the enzymatic nucleic acid molecule consists essentially of a nucleic acid sequence selected from:
a. The nucleic acid sequence as set forth in SEQ. ID. No 1 (DZAR3);
b. The nucleic acid sequence as set forth in SEQ. ID. No. 2 (DZAR18);
c. The nucleic acid sequence as set forth in SEQ. ID. No. 3 (DZAR15);
d. The nucleic acid sequence as set forth in SEQ. ID. No. 4 (DZAR8);
e. The nucleic acid sequence as set forth in SEQ. ID. No. 5 (DZAR34);
f. The nucleic acid sequence as set forth in SEQ. ID. No. 6 (DZAR24);
g. The nucleic acid sequence as set forth in SEQ. ID. No. 7 (DZAR23);
h. The nucleic acid sequence as set forth in SEQ. ID. No. 8 (DZAR28);
i. The nucleic acid sequence as set forth in SEQ. ID. No. 9 (DZAR27);
j. The nucleic acid sequence as set forth in SEQ. ID. No. 10 (DZAR25);
k. The nucleic acid sequence as set forth in SEQ. ID. No. 11 (DZAR7);
l. The nucleic acid sequence as set forth in SEQ. ID. No. 12 (DZAR29);
m. The nucleic acid sequence as set forth in SEQ. ID. No. 13 (DZAR5);
n. The nucleic acid sequence as set forth in SEQ. ID. No. 14 (DZAR9);
o. The nucleic acid sequence as set forth in SEQ. ID. No. 15 (DZAR19); and/or
p. The nucleic acid sequence as set forth in SEQ. ID. No. 16 (DZAR14).

In one embodiment, the enzymatic nucleic acid molecule comprises a nucleic acid sequence selected from:
a) the nucleic acid sequence as set forth in SEQ. ID. No. 4 (DZAR8);
b) the nucleic acid sequence as set forth in SEQ. ID. No. 6 (DZAR24);
c) the nucleic acid sequence as set forth in SEQ. ID. No. 8 (DZAR28); and/or
d) the nucleic acid sequence as set forth in SEQ. ID. No. 11 (DZAR7);
e) a nucleic acid sequence having up to four modifications e.g. 1, 2, 3 or 4 as compared to the nucleic acid sequence as set forth in SEQ. ID. No. 4, 6, 8 or 11.

In one embodiment, the enzymatic nucleic acid molecule consists of a nucleic acid sequence selected from:
a) the nucleic acid sequence as set forth in SEQ. ID. No. 4 (DZAR8);
b) the nucleic acid sequence as set forth in SEQ. ID. No. 6 (DZAR24);
c) the nucleic acid sequence as set forth in SEQ. ID. No. 8 (DZAR28); and/or
d) the nucleic acid sequence as set forth in SEQ. ID. No. 11 (DZAR7);
e) a nucleic acid sequence having up to four modifications e.g. 1, 2, 3 or 4 as compared to the nucleic acid sequence as set forth in SEQ. ID. No. 4, 6, 8 or 11.

In one embodiment, the enzymatic nucleic acid molecule comprises or consists of a nucleic acid sequence as set forth in SEQ. ID. No. 4 (DZAR8).

In one embodiment, the enzymatic nucleic acid molecule comprises or consists of a nucleic acid sequence as set forth in SEQ. ID. No. 6 (DZAR24).

In one embodiment, the enzymatic nucleic acid molecule comprises or consists of a nucleic acid sequence as set forth in SEQ. ID. No. 8 (DZAR28).

In one embodiment, the enzymatic nucleic acid molecule comprises or consists of a nucleic acid sequence as set forth in SEQ. ID. No. 11 (DZAR7).

In one embodiment, the enzymatic nucleic acid molecule comprises at least one of the following modifications:
a) a substituted Locked Nucleic Acid molecule; and/or
b) an inverted-deoxy-thymidine.

In certain embodiments, the inverted-deoxy-thymine is located at the 3'-end of the enzymatic nucleic acid molecule.

In one embodiment, the enzymatic nucleic acid molecule comprises a deoxy-thymidine conjugate.

In certain embodiments, the enzymatic nucleic acid molecule has catalytic activity in the presence of a divalent cation. In a further embodiment, the enzymatic nucleic acid molecule has catalytic activity in the presence of $MgCl^{2+}$. In a further embodiment, the enzymatic nucleic acid molecule has catalytic activity in physiological concentrations of $MgCl^{2+}$, wherein optionally the physiological concentrations are defined as an $MgCl^{2+}$ concentration of between 1 to 4 mM $MgCl^{2+}$.

As disclosed herein, the enzymatic nucleic acid molecule is a DNA enzyme.

In certain embodiments, the enzymatic nucleic acid molecule downregulates the expression of a human Androgen Receptor gene.

In a second aspect of the present invention, there is provided a composition comprising the enzymatic nucleic acid molecule described herein and a pharmaceutically acceptable carrier or diluent. The composition further comprises a divalent cation, wherein optionally the divalent cation is $MgCl^{2+}$. Aptly, the composition as disclosed herein is for use as a medicament.

In one embodiment, the enzymatic nucleic acid molecule or the composition as disclosed herein is for use in the treatment of a cancer. Aptly, the enzymatic nucleic acid molecule or the composition is for use in the treatment of a cancer selected from prostate cancer and breast cancer. Aptly, the enzymatic nucleic acid molecule or the composition is for use in the treatment of prostate cancer.

In certain embodiments, the enzymatic nucleic acid molecule disclosed herein is for use with a divalent cation. Optionally the divalent cation is at physiological concentrations, and further optionally the divalent cation is $MgCl^{2+}$ and the $MgCl^2$ is at a concentration of between 1 to 4 $mM^+$.

In certain embodiments, a delivery agent comprises the enzymatic nucleic acid molecule or the composition as disclosed herein.

In another aspect of the present invention, there is provided a method for the treatment of a cancer, the method comprises administrating a therapeutically effective amount of the enzymatic nucleic acid molecule or the composition as disclosed herein to a subject in need thereof. Aptly, the method is for the treatment of cancer, wherein the subject is suffering from prostate cancer or breast cancer.

In another embodiment, the method comprises administrating a therapeutically effective amount of the enzymatic nucleic acid molecule or the composition, wherein said administration is in the presence of a divalent cation. Aptly, wherein said divalent cation is $MgCl^{2+}$. In a further embodiment, said divalent cation is at physiological concentrations, wherein optionally the physiological concentrations are defined as an $MgCl^{2+}$ concentration of between 1 to 4 mM $MgCl^{2+}$.

In certain embodiments, the enzymatic nucleic acid molecule as disclosed herein is administered associated with a delivery agent. In a further embodiment, the delivery agent is a lipid. Aptly, the lipid is a cationic lipid or a phospholipid or a liposome.

In certain embodiments, the delivery agent is an engineered Adeno-associated virus. In a further embodiment, the method wherein the delivery agent is a nanoparticle.

In certain embodiments, there is provided an expression vector comprising the enzymatic nucleic acid molecule as disclosed herein. Aptly, there is provided a mammalian cell which comprises the expression vector. The mammalian cell may be a human cell.

DETAILED DESCRIPTION OF EMBODIMENTS OF THE INVENTION

Brief Description of the Figures

Embodiments of the present invention will now be described hereinafter, by way of example only, with reference to the accompanying drawings in which:

FIG. 3 illustrates the nucleotide sequences of:
Enzymatic nucleic acid molecule DZAR3 (SEQ. ID. No 1)
Enzymatic nucleic acid molecule DZAR18 (SEQ. ID. No 2)
Enzymatic nucleic acid molecule DZAR15 (SEQ. ID. No 3)
Enzymatic nucleic acid molecule DZAR8 (SEQ. ID. No 4)
Enzymatic nucleic acid molecule DZAR34 (SEQ. ID. No 5)
Enzymatic nucleic acid molecule DZAR24 (SEQ. ID. No 6)
Enzymatic nucleic acid molecule DZAR23 (SEQ. ID. No 7)
Enzymatic nucleic acid molecule DZAR28 (SEQ. ID. No 8)
Enzymatic nucleic acid molecule DZAR27 (SEQ. ID. No 9)
Enzymatic nucleic acid molecule DZAR25 (SEQ. ID. No 10)
Enzymatic nucleic acid molecule DZAR7 (SEQ. ID. No 11)
Enzymatic nucleic acid molecule DZAR29 (SEQ. ID. No 12)
Enzymatic nucleic acid molecule DZAR5 (SEQ. ID. No 13)
Enzymatic nucleic acid molecule DZAR9 (SEQ. ID. No 14)
Enzymatic nucleic acid molecule DZAR19 (SEQ. ID. No 15)
Enzymatic nucleic acid molecule DZAR14 (SEQ. ID. No 16)
Enzymatic nucleic acid molecule DZAR21 (SEQ. ID. No 17)
Enzymatic nucleic acid molecule DZAR33 (SEQ. ID. No 18)
Enzymatic nucleic acid molecule DZAR13 (SEQ. ID. No 19)
Enzymatic nucleic acid molecule DZAR16 (SEQ. ID. No 20)
Enzymatic nucleic acid molecule DZAR1 (SEQ. ID. No 21)
Enzymatic nucleic acid molecule DZAR20 (SEQ. ID. No 22)
Enzymatic nucleic acid molecule DZAR2 (SEQ. ID. No 23)
Enzymatic nucleic acid molecule DZAR26 (SEQ. ID. No 24)
Enzymatic nucleic acid molecule DZAR4 (SEQ. ID. No 25)
Enzymatic nucleic acid molecule DZAR10 (SEQ. ID. No 26)
Enzymatic nucleic acid molecule DZAR11 (SEQ. ID. No 27)
Enzymatic nucleic acid molecule DZAR12 (SEQ. ID. No 28)
Enzymatic nucleic acid molecule DZAR17 (SEQ. ID. No 29)
Enzymatic nucleic acid molecule DZAR22 (SEQ. ID. No 30)
Enzymatic nucleic acid molecule DZAR30 (SEQ. ID. No 31)
Enzymatic nucleic acid molecule DZAR31 (SEQ. ID. No 32)

Enzymatic nucleic acid molecule DZAR32 (SEQ. ID. No 33)

FIG. 3 also illustrates the variable binding arms, as shown in black and the catalytic core which has a consistent sequence (GGCTAGCTACAACGA (SEQ. ID. NO 34)) as shown in red of the enzymatic nucleic acid molecules, in addition to the cleavage efficiency of the above enzymatic nucleic acid molecules, from 0% to 100%.

FIG. 4a) to f) illustrates the efficiency of the enzymatic nucleic acid molecules, specifically designed to target six different regions of the Androgen Receptor RNA (a, 308-352 bp b, 509-548 bp c, 565-604 bp d, 989-1028 bp e, 1304-1343 bp, f, 1496-1535 bp) to cleave FAM-labelled Androgen Receptor RNA. Uncleaved and cleaved RNA was visualised using gel electrophoresis, the cleavage efficiency experiments were carried out in triplicate.

Figure 5:
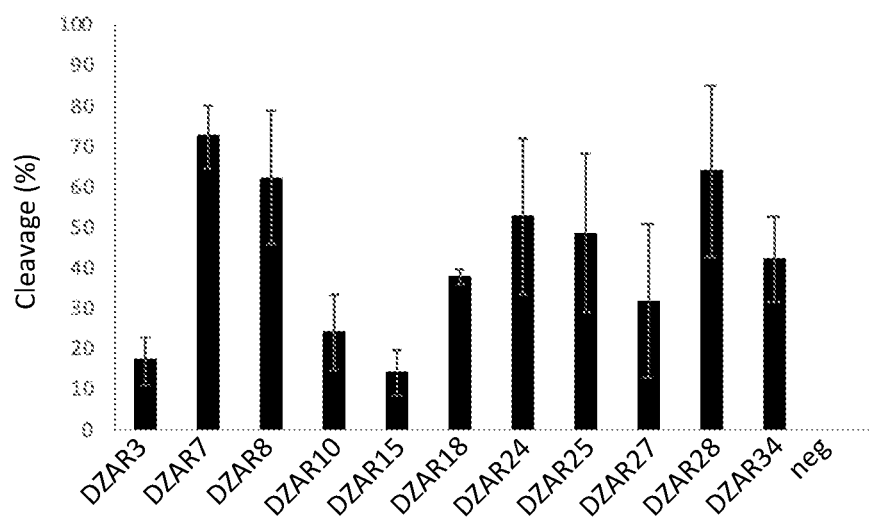

FIG. 5 illustrates the physiologically relevant cleavage capacity of enzymatic nucleic acid molecules: DZAR3, DZAR7, DZAR8, DZAR10, DZAR15, DZAR24, DZAR25, DZAR27, DZAR28 and DZAR34 targeting full-length Androgen Receptor RNA extracted from LNCaP cells. Full-length AR RNA was used to establish a physiological model of RNA cleavage as full-length Androgen Receptor RNA may exhibit differences in RNA folding, in comparison to short pieces of Androgen Receptor RNA. RNA was reversed transcribed into cDNA to perform qPCR analysis, in which qPCR ultimately quantified the Androgen Receptor RNA transcripts. Reactions were carried out in triplicate. Enzymatic nucleic acid molecules DZAR7, DZAR8, DZAR24 and DZAR28 shown superior capabilities to target the full-length Androgen Receptor RNA and had at least 50% cleavage efficiency.

Further details of certain embodiments are provided below.

Throughout the description and claims of this specification, the words "comprise" and "contain" and variations of them mean "including but not limited to" and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of the features and/or steps are mutually exclusive. The invention is not restricted to any details of any foregoing embodiments. The invention extends to any novel one, or novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

The present disclosure relates to the use of an enzymatic nucleic acid molecule to regulate the expression of the human Androgen Receptor. Aspects of the present invention concerns the catalytic cleavage of an Androgen Receptor mRNA by the nuclease activity of an enzymatic nucleic acid molecule.

The term "nucleic acid molecule" or "polynucleotide" shall herein be used interchangeably and be recognized as the polymeric form of nucleotides of any length and comprise of monomers of unmodified or modified nucleotides. If the sugar is a simple ribose, the polymer is RNA (ribonucleic acid) if the sugar is derived from ribose as deoxyribose, the polymer is DNA (deoxyribonucleic acid). As used herein the term "nucleotide" is used as recognised in the art to refer to a molecule comprising a five-carbon sugar, a phosphate group and a nitrogenous heterocyclic base. The term "nucleotide" shall be understood to include both natural nucleotides, such as ribose and deoxyribose as well as chemically or biochemically modified, non-natural, and/or derivatized nucleotides. The nucleotides can be unmodified or modified at the sugar, phosphate and/or base moiety.

As used herein, the term "enzymatic nucleic acid molecule" refers to a nucleic acid molecule of varying lengths and folding patterns, which has complementarity to a specified RNA target, and also has an enzymatic activity which is active to specifically cleave target RNA. Certain embodiments of the present invention may alternatively be described as having nuclease or ribonuclease activity, and these terms may be used interchangeably herein. The enzymatic nucleic acid molecule is able to intermolecularly cleave RNA and thereby inactivate a target RNA molecule. The complementary regions allow sufficient hybridization of the enzymatic nucleic acid molecule to the target RNA to facilitate cleavage of said RNA target by the intermolecular nuclease activity. The term "enzymatic nucleic acid molecule" encompasses natural and modified nucleotides and also other known terms in the art such as "deoxyribozyme" or "catalytic DNA molecule" or "DNAzyme". An enzymatic nucleic acid molecule may be produced synthetically or be derived from organisms or other sources.

Aptly, the enzymatic nucleic acid molecule is a DNA molecule.

The enzymatic nucleic acid molecules described herein may comprise modified nucleic acids. As used herein the term "modified nucleotide" and "modified nucleic acid molecule" refers to all known modified nucleotides known in the art both naturally occurring and artificial such as chemically or biochemically modified, non-natural, or derivatized nucleotides.

One example of a modified nucleotide is a "locked nucleotide". As used herein, the term "locked nucleotide" refers to modified nucleotides included in a polymer defined as a "locked nucleic acid molecule". The ribose moiety of a locked nucleic acid nucleotide is modified with an extra bridge connecting the 2' and 4' carbons. The bridge "locks" the ribose in the 3'-endo structural conformation, which is often found in the A-form of DNA or RNA. Locked nucleic acid molecule nucleotides can be mixed with DNA or RNA or modified derivates there of forming a polymer. The locked ribose conformation may enhance base stacking and backbone pre-organization. This may increase the thermal stability of the polynucleotide.

Another example of a modified nucleic acid molecule includes the introduction of an inverted deoxy-thymidine (dT). Oligonucleotides can be designed to incorporate 5' to 5' or 3' to 3' linkages. Inverted dT can be introduced at the 3'-end of an oligonucleotide to create a 3' to 3' linkage which creates unique characteristics which include but are not limited to preventing DNA polymerase from further extending the DNA sequence and protecting the oligonucleotide from 3' exonuclease cleavage.

In certain embodiments, an enzymatic nucleic acid molecule comprises at least one complementary nucleic acid region which may be capable of hybridizing, preferably in physiological conditions, to nucleotide sequences encoding a full-length Androgen Receptor polypeptide as disclosed herein. Androgen Receptor variant polypeptides may be those that are encoded by an Androgen Receptor variant polynucleotide including for example polynucleotides which encode splice variants including those described herein. As used herein, the term "Androgen Receptor" refers to an intracellular protein steroid receptor of the nuclear receptor super-family that recognizes hormones, specifically, hormones of the androgen family such as, but not limited to, testosterone and dihydrotestosterone. The enzymatic nucleic acid molecules described herein hybridize to a human androgen receptor.

Encompassed in the term "Androgen Receptor" are mutant and splice variant forms of an Androgen Receptor. Mutants include Androgen Receptor proteins with amino acid additions, insertions, truncations and deletions. An example of Androgen Receptor splice variants are truncations such as, but not limited to, AR-V1, AR-V2, AR-V3, AR-V4, AR-V5, AR-V567es, AR-V6 or AR-V7. Further Androgen Receptor mutations present as point mutations, examples of point mutations are, but not limited to, T877A, D879G, W741C, W741L, M749L, R629Q, G124V, P533S, T575A, H874Y or F876L. Mutated variants of an Androgen Receptor may gain the ability to associate with a wider range of ligands, often referred to within the art as ligand promiscuity, thus allowing binding and activation of the Androgen Receptor and its subsequent signalling pathway by other physiologically relevant hormones. An amino acid sequence of the human AR can be found under Accession No. P10275 version 3 (UniProtKB). Various splice variants are known as indicated in P10275 version 3.

In some embodiments, the enzymatic nucleic acid prevents or reduces expression of the Androgen Receptor. As used herein, the term "expression" refers to the process of converting genetic information encoded in a gene into RNA (e.g., mRNA, rRNA, tRNA, or snRNA) through "transcription" of the gene and for protein encoding genes, into protein through "translation" of mRNA. Gene expression can be regulated at many stages in the process. "Down-regulation" or "repression" refers to regulation that decrease production of the coded protein. In one embodiment, the present invention relates to an enzymatic nucleic acid molecule comprising a catalytic region comprising about 15 nucleic acid residues, wherein the catalytic region is capable of cleaving an mRNA molecule.

In a further embodiment, the catalytic activity of said enzymatic nucleic acid molecule may occur at physiological conditions.

In one embodiment, an enzymatic nucleic acid molecule comprises at least one complementary nucleic acid region which may be capable of hybridizing, preferably in physiological conditions, to nucleotide sequences encoding a full-length Androgen Receptor polypeptide obtained from LNCaP cells. As disclosed herein, LNCaP cells refers to an androgen sensitive, prostate cancer cell line.

In certain embodiments of the present invention the enzymatic nucleic acid molecule comprises at least one complementary nucleic acid region with a sequence identity that is complementary to a sequence of target nucleic acid molecule. As defined herein the complementary region of an enzymatic nucleic acid molecule has at least about 80% nucleic acid sequence identity with a nucleic acid sequence of a full-length native nucleic acid sequence encoding a full-length native polypeptide.

Ordinarily, an enzymatic nucleic acid molecule comprising at least one complementary nucleic acid region comprising a nucleic acid sequence identity of at least 80%, alternatively at least about 81%, 82%, 83%, 84%, 85%, 86%, 87%, 88%, 89%, 90%, 91%, 92%, 93%, 94%, 95%, 96%, 97%, 98%, or 99% nucleic acid sequence identity with a nucleic acid sequence encoding a full-length native sequence.

The terms "sequence identity", "percent identity" and "sequence percent identity" in the context of two or more nucleic acids or polypeptides, refer to two or more sequences or subsequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity can be measured using sequence comparison software or algorithms or by visual inspection. Various algorithms and software are known in the art that can be used to obtain alignments of amino acid or nucleotide sequences.

Suitable programs to determine percent sequence identity include for example the BLAST suite of programs available from the U.S. government's National Center for Biotechnology Information BLAST web site (http://blast.ncbi.nlm-.nih.gov/Blast.cgi). Comparisons between two sequences can be carried using either the BLASTN or BLASTP algorithm. BLASTN is used to compare nucleic acid sequences, while BLASTP is used to compare amino acid sequences. ALIGN, ALIGN-2 (Genentech, South San Francisco, California) or MegAlign, available from DNASTAR, are additional publicly available software programs that can be used to align sequences. One skilled in the art can determine appropriate parameters for maximal alignment by particular alignment software. In certain embodiments, the default parameters of the alignment software are used.

In certain embodiments of the present invention, the biological activity of the enzymatic nucleic acid molecule is retained in physiological conditions.

In some embodiments, the enzymatic nucleic acid molecule is for use with a divalent cation. As used here in the term "divalent cation" is used to refer to an ion, specifically a cation with a valence of two, wherein valence denotes the electrons available for chemical bond formation. In certain embodiments, the divalent cation is $MgCl_2$. Aptly, the divalent cation is an in vivo endogenous divalent cation.

As used herein, the term "physiologic conditions" refers to reaction conditions emulating those found intracellularly in mammalian organisms, particularly humans. Variations in temperature, availability of cations, and pH ranges may be covered where referring to physiologic conditions. It is known in the art physiological conditions comprise a temperature of about 35°-40° C. as well as a pH of about 7.0-8.0 and further comprise the availability of cations, preferably divalent with a concentration of about 2-15 mM $MgCl_2$ being particularly preferred.

In certain embodiments of the present invention, the Androgen Receptor protein expression may be repressed upon the degradation of its mRNA.

In a further aspect of the present invention, there is a composition comprising an enzymatic nucleic acid molecule as described herein. In certain embodiments, the composition is a pharmaceutical composition and is for administration to a subject. In certain embodiments, the subject is a mammalian subject. In certain embodiments, the subject is a human.

As used herein, the term "treating" includes alleviating the symptoms of the condition and may relate to alleviating such symptoms e.g. reducing or preventing the occurrence of the symptoms. Reducing in this context may refer to the reducing in the severity and/or occurrence of one or more symptoms for example reducing the resistance of prostate cancer, and other Androgen Receptor diseases, to hormone therapy. The treatment of a disease with an enzymatic nucleic acid molecule as described herein may require the administering of a therapeutically effective amount of a composition by a professional skilled in the art. In one embodiment of the present invention, the enzymatic nucleic acid molecule may be used to treat Androgen Receptor dependent disease such as, but not limited to, breast cancer, prostate cancer, ovarian cancer, bladder cancer, pancreatic cancer and polycystic ovary disease.

In certain embodiments, the present invention refers to a method for the treatment of cancer comprising administration an enzymatic nucleic acid molecule described herein. As defined herein, cancer refers to a malignant tumour which may be selected from the group consisting of: solid tumours such as melanoma, skin cancers, small cell lung cancer, non-small cell lung cancer, glioma, hepatocellular (liver) carcinoma, gallbladder cancer, thyroid tumour, bone cancer, gastric (stomach) cancer, prostate cancer, breast cancer, ovarian cancer, cervical cancer, uterine cancer, vulval cancer, endometrial cancer, testicular cancer, bladder cancer, lung cancer, glioblastoma, endometrial cancer, kidney cancer, renal cell carcinoma, colon cancer, colorectal, pancreatic cancer, oesophageal cancer, brain/CNS cancers, head and neck cancers, neuronal cancers, mesothelioma, sarcomas, biliary (cholangiocarcinoma), small bowel adenocarcinoma, paediatric malignancies, epidermoid carcinoma, sarcomas, cancer of the pleural/peritoneal membranes and leukaemia, including acute myeloid leukaemia, acute lymphoblastic leukaemia, and multiple myeloma.

In certain embodiments, the present invention relates to a method for the treatment of prostate cancer. The term "prostate cancer," as used herein, refers to a malignant tumour of glandular origin in the prostate gland. In certain embodiments, the subject is male e.g. a male human.

In a further embodiment, the present invention may be used for the treatment of advanced stage also referred to as castrate-resistant prostate cancer. As used herein the term "castrate-resistant" describes prostate cancer disease progression despite androgen/hormone depletion therapy and may present as either a continuous rise in serum prostate-specific antigen levels, the progression of pre-existing disease, and/or the appearance of new metastases. In certain embodiments of the present invention, the pharmaceutical composition comprises a pharmaceutically acceptable diluent. As used herein the term "pharmaceutically acceptable diluent" is defined as a water or other pharmaceutically acceptable aqueous solution containing one or more pharmaceutically acceptable excipients for use in making the compositions of certain embodiments of the invention.

In certain embodiments, the method for the treatment of cancer comprises administrating a therapeutically effective amount of the enzymatic nucleic acid molecule as disclosed herein. The term "administration" as used herein, refers to any method which, in sound medical practice, delivers the medicament to the subject to be treated such as to be effective in treating the disease.

In certain embodiments, the enzymatic nucleic acid molecule described herein may be for use in the treatment of polycystic ovarian syndrome in a subject. In certain embodiments, the subject is female e.g. a female human.

The delivery of a medicament may be facilitated by the use of a delivery agent. Aptly the delivery agent is a molecule/s that facilitates the delivery of a therapeutically effective amount of the composition. The term "delivery agent" is an art-recognized term and includes molecules that facilitate the intracellular delivery of a therapeutic agent or other material. Examples of delivery agents include: lipids (e.g., a cationic lipid, virosome or liposome), nanoparticles, biomaterial nano-carriers and/or viral vectors such as adeno-associated virus vector. In certain embodiments, the delivery agent may be an aptamer or a nanostructure formed from a biomaterial. In certain embodiments, the delivery agent is a biomaterial nano-carrier.

As used herein, the terms "therapeutically effective amount" refers to an amount sufficient to provide a therapeutic or healthful benefit in the context of cancer. The exact dose administered will depend on the purpose of the treatment and will be determined by one skilled in the art using known techniques. In sensitized cells, the therapeutically effective dose can often be lower than the conventional therapeutically effective dose for non-sensitized cells such as castrate-resistant prostate cancer. Wherein "sensitized cells" are defined as expressing an Androgen Receptor that requires its hormone substrate for activation.

EXAMPLES

Tumour development often presents a challenge to anti-cancer treatment due to tumour micro-evolution mediating treatment resistance. The following examples are focused on determining whether the reagents of certain embodiments of the present invention could be used to prevent tumour-induced resistance to prostate cancer treatment.

Design of Anti-Androgen Receptor Enzymatic Nucleic Acids

Figure 1:
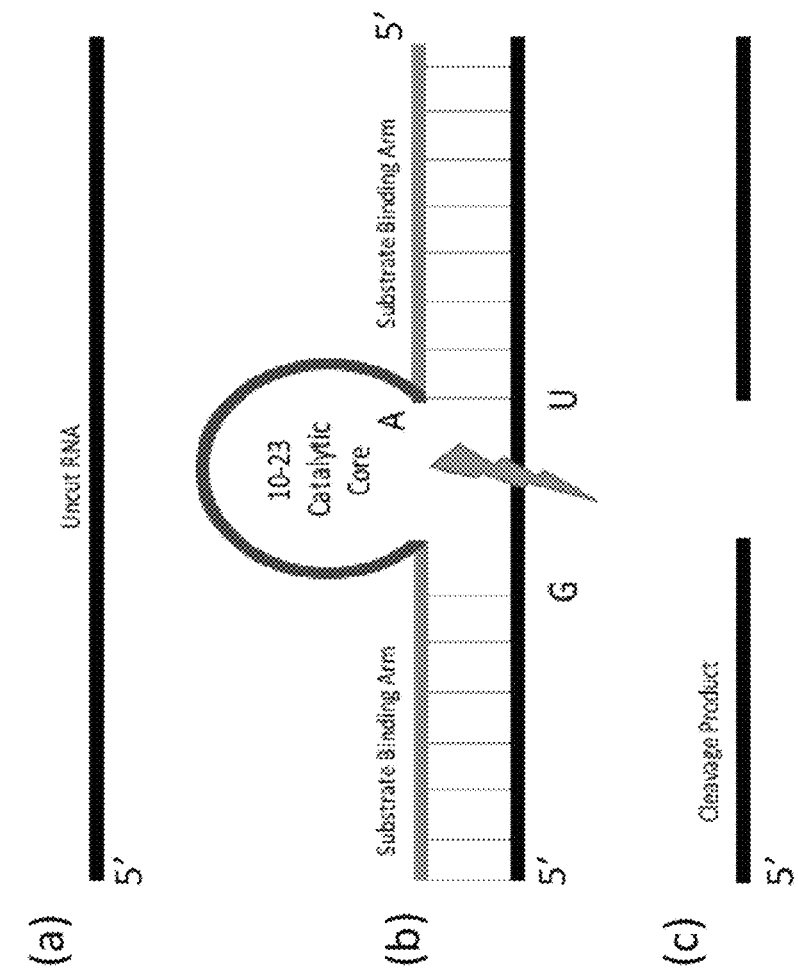
FIG. 1 illustrates a schematic representation of an anti-Androgen Receptor (AR) enzymatic nucleic acid molecule according to certain embodiments of the invention. The human Androgen Receptor sequence was obtained from the National Centre for Bioscience Information (NCBI). Each enzymatic nucleic acid molecule was designed to target a specific RNA molecule in vitro via incorporation of two fixed-sequence 5' and 3' binding arms designed to target various regions of this sequence via Watson-Crick interactions. Each enzymatic nucleic acid molecule comprises a 10-23 DNAzyme catalytic core which actively cleaves the target AR RNA.
Figure 2:
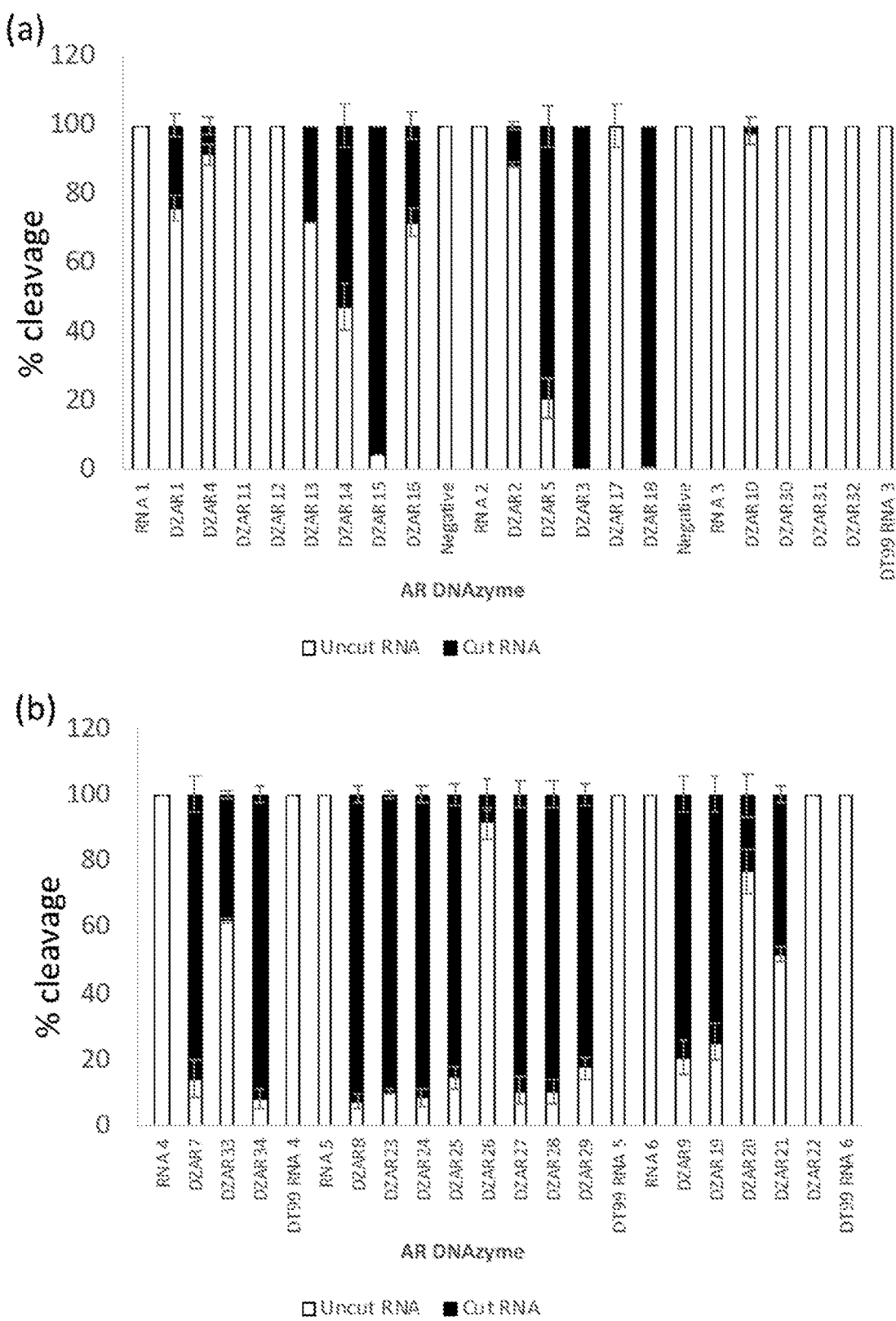
FIGS. 2*a* and *b* illustrate the cleavage of synthesised Androgen Receptor mRNA by various enzymatic nucleic acid molecules. Densitometry was performed and the percentage of cleavage permitted by the various enzymatic nucleic acid molecules was calculated, the cleavage efficiency experiments were carried out in triplicate.

The Androgen Receptor (AR) sequence used in the cleavage experiments shown in FIG. 2 was obtained from the National Centre for Bioscience Information (NCBI). Each enzymatic nucleic acid molecule was designed to target a specific RNA molecule via incorporation of 5' and 3' binding arms which target various regions of AR RNA via Watson-Crick interactions. Each enzymatic nucleic acid molecule comprises a 10-23 DNAzyme catalytic core which actively cleaves the target AR RNA via a transesterification reaction between a purine-pyrimidine dinucleotide motif.

Example 1—Cleavage of AR RNA Fragments

Analysis of cleavage efficiency of various enzymatic nucleic acid molecules was determined by initially diluting the enzymatic nucleic acid molecules to a final concentration of 1 µM, in buffer containing 50 mM Tris-HCL (pH 7.5), 10 mM $MgCl_2$, 150 Mm NaCl and 0.01% SDS. The RNA was diluted to a final concentration of 0.2 µM. The enzymatic nucleic acid molecules were then incubated with Fluorescein amidite (FAM)-labelled Androgen Receptor RNA fragments for two hours before being terminated by the addition of RNA loading dye (NEB) and being snap frozen on dry ice. A non-targeting DNAZyme was used as a negative control (−).

Results of Example 1 are shown in FIG. 2. It was observed in the in vitro cleavage experiments using short-stranded fragments of AR RNA that various enzymatic nucleic acid molecules cleave with superior efficiency, compared to others. In particular, DZAR3 and DZAR18 mediated around 100% cleavage of target RNA.

Gel Electrophoresis

Samples were then boiled at 70° C. prior to separation using urea PAGE 15% gel to denature the secondary RNA structures and fragments were visualised on a Fusion FX detection system.

Densitometry

Gel images were analysed using ImageJ and densitometry performed to quantify the uncleaved and cleaved products. The percentage of cleavage permitted by the enzymatic nucleic acid molecules was calculated.

Example 2—Cleavage of Full Length AR RNA

LNCaP cells (ATCC) were cultured in Roswell Park Memorial Institute ((RMPI) 1640, supplemented with 2 mM I-Glutamine, 10% streptomycin and Phenyl Red (PSG), 10% fetal bovine serum (FBS), Biosera). Cells were cultured at 37° C. and 5% Carbon Dioxide and passaged at 80% confluency.

The cleavage capacity of enzymatic nucleic acid molecules, DZAR3, DZAR7, DZAR8, DZAR10, DZAR15, DZAR24, DZAR25, DZAR27, DZAR28 and DZAR34 targeting full-length Androgen Receptor RNA extracted from LNCaP cells was determined. Total RNA was extracted from LNCaP cells using an RNA extraction kit (RBC Bioscience). 500 ng of total AR RNA was utilised in cleavage reactions. Samples were then diluted using RNase-free water and RNA was reversed transcribed into cDNA to perform qPCR analysis (LightCycler, Roche), in which qPCR ultimately quantified the Androgen Receptor RNA transcripts. Data was normalised to an internal control (L19) and relative expression was calculated using the $2^{-\Delta\Delta Ct}$ method.

Figure 4:
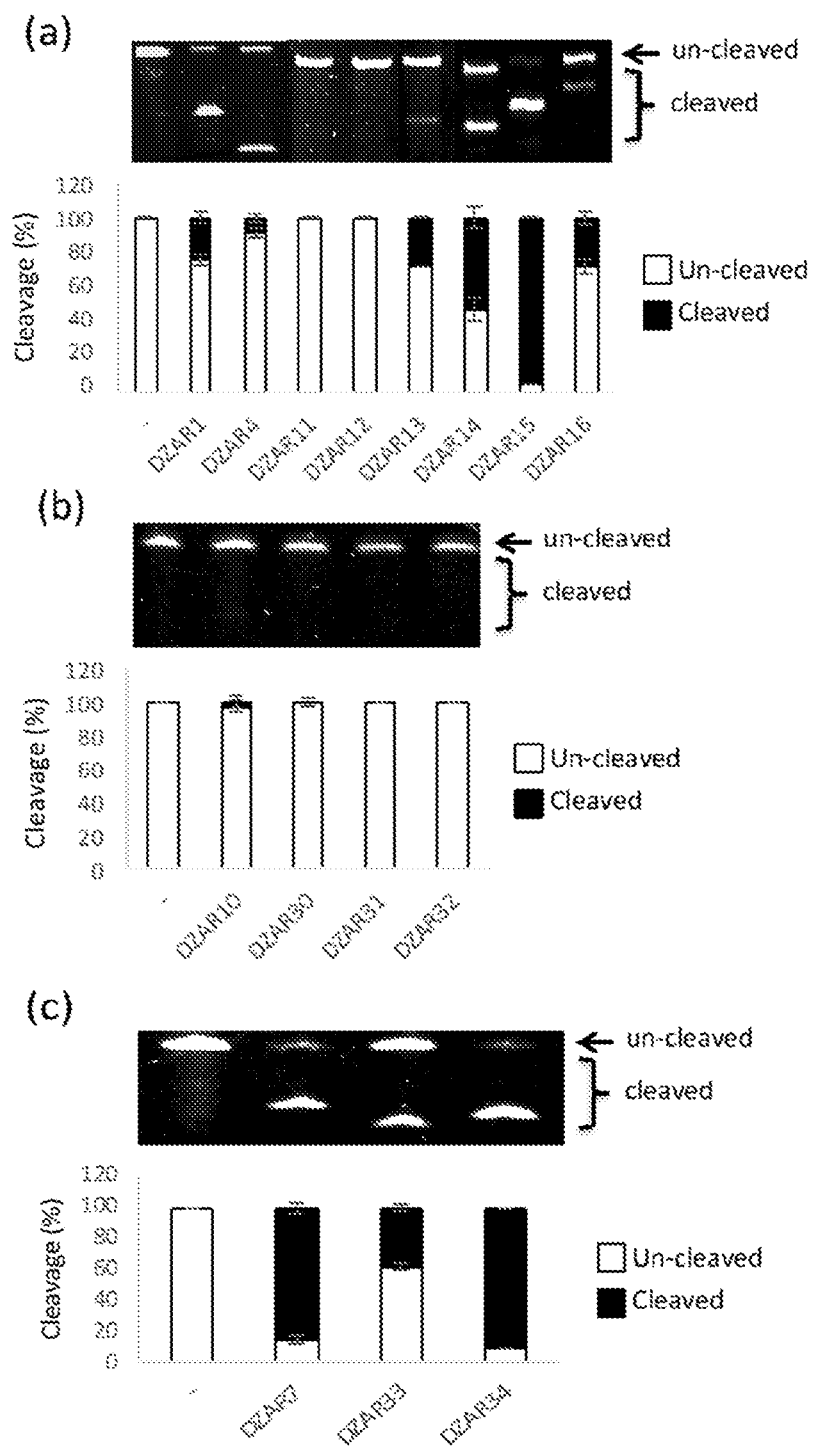
Figure 4:
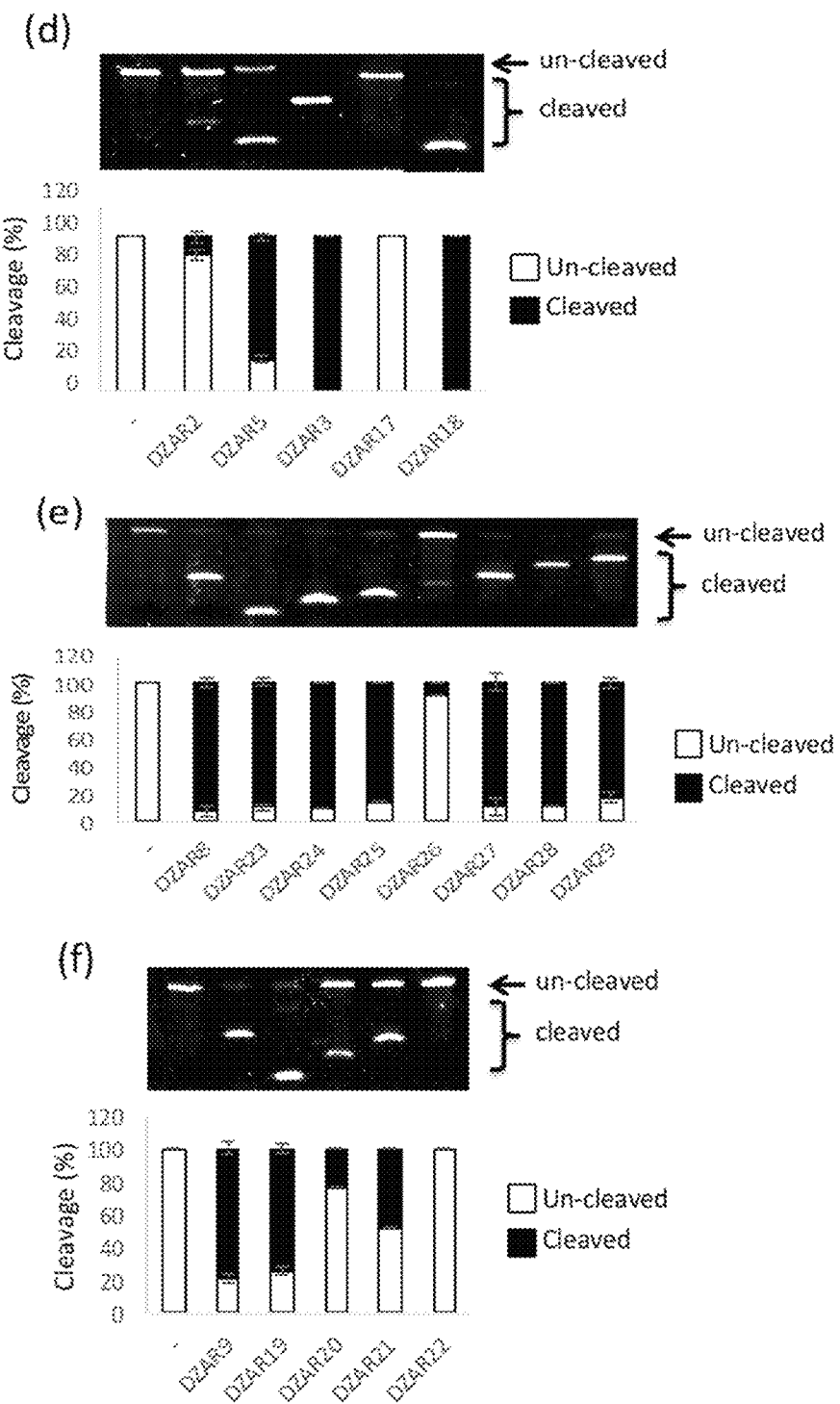

Results of Example 2 are shown in FIG. 4. FIG. 4 illustrates the cleavage efficiency of enzymatic nucleic acid molecules targeting total RNA extracted from LNCaP cells and thus full-length AR RNA. It was found that various enzymatic nucleic acid molecules have superior cleavage capacity in comparison to others. Interestingly, DZAR7, DZAR8, DZAR24 and DZAR28 showed the highest cleavage efficiency, exhibiting cleavage greater than 50%.

The invention claimed is:

1. An enzymatic nucleic acid molecule which regulates the expression of a human Androgen Receptor gene, wherein the enzymatic nucleic acid molecule comprises a nucleic acid sequence having at least 80% sequence identity to a nucleic acid sequence selected from:
   a. The nucleic acid sequence set forth in SEQ. ID. No 1 (DZAR3)
   b. The nucleic acid sequence set forth in SEQ. ID. No 2 (DZAR18)
   c. The nucleic acid sequence set forth in SEQ. ID. No 3 (DZAR15)
   d. The nucleic acid sequence set forth in SEQ. ID. No 4 (DZAR8)
   e. The nucleic acid sequence set forth in SEQ. ID. No 5 (DZAR34)
   f. The nucleic acid sequence set forth in SEQ. ID. No 6 (DZAR24)
   g. The nucleic acid sequence set forth in SEQ. ID. No 7 (DZAR23)
   h. The nucleic acid sequence set forth in SEQ. ID. No 8 (DZAR28)
   i. The nucleic acid sequence set forth in SEQ. ID. No 9 (DZAR27)
   j. The nucleic acid sequence set forth in SEQ. ID. No 10 (DZAR25)
   k. The nucleic acid sequence set forth in SEQ. ID. No 11 (DZAR7)
   l. The nucleic acid sequence set forth in SEQ. ID. No 12 (DZAR29)
   m. The nucleic acid sequence set forth in SEQ. ID. No 13 (DZAR5)
   n. The nucleic acid sequence set forth in SEQ. ID. No 14 (DZAR9)
   o. The nucleic acid sequence set forth in SEQ. ID. No 15 (DZAR19)
   p. The nucleic acid sequence set forth in SEQ. ID. No 16 (DZAR14)
   q. The nucleic acid sequence set forth in SEQ. ID. No 17 (DZAR21)
   r. The nucleic acid sequence set forth in SEQ. ID. No 18 (DZAR33)
   s. The nucleic acid sequence set forth in SEQ. ID. No 19 (DZAR13)
   t. The nucleic acid sequence set forth in SEQ. ID. No 20 (DZAR16)
   u. The nucleic acid sequence set forth in SEQ. ID. No 21 (DZAR1)
   v. The nucleic acid sequence set forth in SEQ. ID. No 22 (DZAR20)
   w. The nucleic acid sequence set forth in SEQ. ID. No 23 (DZAR2)
   x. The nucleic acid sequence set forth in SEQ. ID. No 24 (DZAR26)
   y. The nucleic acid sequence set forth in SEQ. ID. No 25 (DZAR4)

z. The nucleic acid sequence set forth in SEQ. ID. No 26 (DZAR10)
aa. The nucleic acid sequence set forth in SEQ. ID. No 27 (DZAR11)
bb. The nucleic acid sequence set forth in SEQ. ID. No 28 (DZAR12)
cc. The nucleic acid sequence set forth in SEQ. ID. No 29 (DZAR17)
dd. The nucleic acid sequence set forth in SEQ. ID. No 30 (DZAR22)
ee. The nucleic acid sequence set forth in SEQ. ID. No 31 (DZAR30)
ff. The nucleic acid sequence set forth in SEQ. ID. No 32 (DZAR31)
gg. The nucleic acid sequence set forth in SEQ. ID. No 33 (DZAR32); and/or the enzymatic nucleic acid molecule consists of a nucleic acid sequence having at least 80% sequence identity to a nucleic acid sequence selected from:
a. The nucleic acid sequence set forth in SEQ. ID. No 1 (DZAR3)
b. The nucleic acid sequence set forth in SEQ. ID. No 2 (DZAR18)
c. The nucleic acid sequence set forth in SEQ. ID. No 3 (DZAR15)
d. The nucleic acid sequence set forth in SEQ. ID. No 4 (DZAR8)
e. The nucleic acid sequence set forth in SEQ. ID. No 5 (DZAR34)
f. The nucleic acid sequence set forth in SEQ. ID. No 6 (DZAR24)
g. The nucleic acid sequence set forth in SEQ. ID. No 7 (DZAR23)
h. The nucleic acid sequence set forth in SEQ. ID. No 8 (DZAR28)
i. The nucleic acid sequence set forth in SEQ. ID. No 9 (DZAR27)
j. The nucleic acid sequence set forth in SEQ. ID. No 10 (DZAR25)
k. The nucleic acid sequence set forth in SEQ. ID. No 11 (DZAR7)
l. The nucleic acid sequence set forth in SEQ. ID. No 12 (DZAR29)
m. The nucleic acid sequence set forth in SEQ. ID. No 13 (DZAR5)
n. The nucleic acid sequence set forth in SEQ. ID. No 14 (DZAR9)
o. The nucleic acid sequence set forth in SEQ. ID. No 15 (DZAR19)
p. The nucleic acid sequence set forth in SEQ. ID. No 16 (DZAR14)
q. The nucleic acid sequence set forth in SEQ. ID. No 17 (DZAR21)
r. The nucleic acid sequence set forth in SEQ. ID. No 18 (DZAR33)
s. The nucleic acid sequence set forth in SEQ. ID. No 19 (DZAR13)
t. The nucleic acid sequence set forth in SEQ. ID. No 20 (DZAR16)
u. The nucleic acid sequence set forth in SEQ. ID. No 21 (DZAR1)
v. The nucleic acid sequence set forth in SEQ. ID. No 22 (DZAR20)
w. The nucleic acid sequence set forth in SEQ. ID. No 23 (DZAR2)
x. The nucleic acid sequence set forth in SEQ. ID. No 24 (DZAR26)
y. The nucleic acid sequence set forth in SEQ. ID. No 25 (DZAR4)
z. The nucleic acid sequence set forth in SEQ. ID. No 26 (DZAR10)
aa. The nucleic acid sequence set forth in SEQ. ID. No 27 (DZAR11)
bb. The nucleic acid sequence set forth in SEQ. ID. No 28 (DZAR12)
cc. The nucleic acid sequence set forth in SEQ. ID. No 29 (DZAR17)
dd. The nucleic acid sequence set forth in SEQ. ID. No 30 (DZAR22)
ee. The nucleic acid sequence set forth in SEQ. ID. No 31 (DZAR30)
ff. The nucleic acid sequence set forth in SEQ. ID. No 32 (DZAR31)
gg. The nucleic acid sequence set forth in SEQ. ID. No 33 (DZAR32).

2. The enzymatic nucleic acid molecule as claimed in claim 1, comprising a catalytic region comprising about 15 nucleic acid residues, wherein the catalytic region is capable of cleaving an mRNA molecule and/or the enzymatic nucleic acid molecule comprises at least one region wherein said region comprises a sequence which is complementary to a nucleic acid sequence comprised in an Androgen Receptor mRNA molecule.

3. The enzymatic nucleic acid molecule as claimed in claim 2, which comprises two regions which each comprise a sequence which is complementary to a nucleic acid sequence comprised in an Androgen Receptor mRNA molecule, wherein optionally the enzymatic nucleic acid molecule comprises a first region which comprises a sequence which is complementary to a nucleic acid sequence comprised in an Androgen Receptor mRNA molecule at a 5' end of the catalytic region and a second region which comprises a sequence which is complementary to a nucleic acid sequence comprised in an Androgen Receptor mRNA molecule at a 3' end of the catalytic core.

4. The enzymatic nucleic acid molecule as claimed in claim 1, comprising one or more modified nucleic acid residues and/or one of more unnatural nucleic acid residues, wherein optionally the enzymatic nucleic acid molecule comprises at least one Locked Nucleic Acid residue.

5. The enzymatic nucleic acid molecule as claimed in claim 1, which upon hybridisation to an Androgen Receptor RNA molecule catalytically cleaves said RNA molecule, optionally wherein the catalytic cleavage event is at least about 50%, 55%, 60%, 65%, 70%, 75%, 80%, 85%, 90%, 91%, 92%, 93%, 94%, 95%, 96%, 97%, 98%, 99% or 100%) cleavage efficiency, wherein optionally the enzymatic nucleic acid molecule catalytically cleaves at least 50% of Androgen Receptor RNA extracted from LNCaP cells.

6. The enzymatic nucleic acid molecule as claimed in claim 1,
wherein the enzymatic nucleic acid comprises a nucleic acid sequence selected from:
a. The nucleic acid sequence as set forth in SEQ. ID. No 1 (DZAR3)
b. The nucleic acid sequence as set forth in SEQ. ID. No. 2 (DZAR18)
c. The nucleic acid sequence as set forth in SEQ. ID. No. 3 (DZAR15)
d. The nucleic acid sequence as set forth in SEQ. ID. No. 4 (DZAR8)
e. The nucleic acid sequence as set forth in SEQ. ID. No. 5 (DZAR34)

f. The nucleic acid sequence as set forth in SEQ. ID. No. 6 (DZAR24)
g. The nucleic acid sequence as set forth in SEQ. ID. No. 7 (DZAR23)
h. The nucleic acid sequence as set forth in SEQ. ID. No. 8 (DZAR28)
i. The nucleic acid sequence as set forth in SEQ. ID. No. 9 (DZAR27)
j. The nucleic acid sequence as set forth in SEQ. ID. No. 10 (DZAR25)
k. The nucleic acid sequence as set forth in SEQ. ID. No. 11 (DZAR7)
l. The nucleic acid sequence as set forth in SEQ. ID. No. 12 (DZAR29)
m. The nucleic acid sequence as set forth in SEQ. ID. No. 13 (DZAR5)
n. The nucleic acid sequence as set forth in SEQ. ID. No. 14 (DZAR9)
o. The nucleic acid sequence as set forth in SEQ. ID. No. 15 (DZAR19)
p. The nucleic acid sequence as set forth in SEQ. ID. No. 16 (DZAR14)
q. or a sequence having up to four modifications as compared to the nucleic acid sequence as set forth in SEQ. ID. No. 1, 2, 3, 4, 5, 6, 7, 8, 9, 10, 11, 12, 13, 14, 15, or 16.

7. The enzymatic nucleic acid molecule as claimed in claim 6, which consists of a nucleic acid sequence selected from:
r. The nucleic acid sequence as set forth in SEQ. ID. No 1 (DZAR3)
s. The nucleic acid sequence as set forth in SEQ. ID. No. 2 (DZAR18)
t. The nucleic acid sequence as set forth in SEQ. ID. No. 3 (DZAR15)
u. The nucleic acid sequence as set forth in SEQ. ID. No. 4 (DZAR8)
v. The nucleic acid sequence as set forth in SEQ. ID. No. 5 (DZAR34)
w. The nucleic acid sequence as set forth in SEQ. ID. No. 6 (DZAR24)
x. The nucleic acid sequence as set forth in SEQ. ID. No. 7 (DZAR23)
y. The nucleic acid sequence as set forth in SEQ. ID. No. 8 (DZAR28)
z. The nucleic acid sequence as set forth in SEQ. ID. No. 9 (DZAR27)
aa. The nucleic acid sequence as set forth in SEQ. ID. No. 10 (DZAR25)
bb. The nucleic acid sequence as set forth in SEQ. ID. No. 11 (DZAR7)
cc. The nucleic acid sequence as set forth in SEQ. ID. No. 12 (DZAR29)
dd. The nucleic acid sequence as set forth in SEQ. ID. No. 13 (DZAR5)
ee. The nucleic acid sequence as set forth in SEQ. ID. No. 14 (DZAR9)
ff. The nucleic acid sequence as set forth in SEQ. ID. No. 15 (DZAR19)
gg. The nucleic acid sequence as set forth in SEQ. ID. No. 16 (DZAR14);

wherein optionally the enzymatic nucleic acid molecule comprises or consists of a nucleic acid molecule having a nucleic acid sequence as set forth in: SEQ. ID. No. 4 (DZAR8); SEQ. ID. No. 6 (DZAR24); SEQ. ID. No. 8 (DZAR28) or SEQ. ID. No. 11 (DZAR7).

8. The enzymatic nucleic acid molecule as claimed in claim 1, which comprises at least one of the following modifications:
   a) a substituted Locked Nucleic Acid molecule; and/or
   b) an inverted-deoxy-thymidine located at the 3'-end of an oligonucleotide; wherein optionally the nucleic acid molecule comprises a deoxy-thymidine conjugate.

9. The enzymatic nucleic acid molecule as claimed in claim 1, that has catalytic activity in the presence of a divalent cation, wherein optionally the enzymatic nucleic acid molecule has catalytic activity in the presence of $MgCl2+$, optionally wherein the enzymatic nucleic acid molecule has catalytic activity in physiological concentrations of $MgCl2+$, wherein optionally the physiological concentrations are defined as an $MgCl2+$ concentration of between 1 to 4 mM $MgCl2+$.

10. The enzymatic nucleic acid molecule as claimed in claim 7, which is a DNA enzyme and/or which downregulates the expression of a human Androgen Receptor gene.

* * * * *